(12) United States Patent
Hirokawa et al.

(10) Patent No.: US 8,003,359 B2
(45) Date of Patent: Aug. 23, 2011

(54) EUKARYOTIC AMADORIASE HAVING EXCELLENT THERMAL STABILITY, GENE AND RECOMBINANT DNA FOR THE EUKARYOTIC AMADORIASE, AND PROCESS FOR PRODUCTION OF EUKARYOTIC AMADORIASE HAVING EXCELLENT THERMAL STABILITY

(75) Inventors: Kozo Hirokawa, Noda (JP); Atsushi Ichiyanagi, Noda (JP)

(73) Assignee: Kikkoman Corporation, Noda-Shi, Chiba (JP)

( * ) Notice: Subject to any disclaimer, the term of this patent is extended or adjusted under 35 U.S.C. 154(b) by 47 days.

(21) Appl. No.: 12/300,658

(22) PCT Filed: Apr. 17, 2007

(86) PCT No.: PCT/JP2007/058304
§ 371 (c)(1),
(2), (4) Date: Jun. 4, 2009

(87) PCT Pub. No.: WO2007/125779
PCT Pub. Date: Nov. 8, 2007

(65) Prior Publication Data
US 2009/0239239 A1    Sep. 24, 2009

(30) Foreign Application Priority Data

Apr. 25, 2006    (JP) .................................. 2006-120363

(51) Int. Cl.
*C12N 9/02* (2006.01)
*C12N 9/00* (2006.01)
*C07H 21/04* (2006.01)
(52) U.S. Cl. .......................... 435/189; 435/183; 536/23.2
(58) Field of Classification Search .................. 435/189, 435/183; 536/23.2
See application file for complete search history.

(56) References Cited

U.S. PATENT DOCUMENTS 7,018,823 B2 *    3/2006    Kurosawa et al. ............ 435/189

FOREIGN PATENT DOCUMENTS

| EP | 1 291 416 | 3/2003 |
|---|---|---|
| EP | 1 344 828 | 9/2003 |
| EP | 1 626 088 | 2/2006 |
| JP | 61-280297 B2 | 12/1986 |
| JP | 7289253 A | 11/1995 |
| JP | 8336386 A | 12/1996 |
| JP | 11127895 A | 5/1999 |
| JP | 11155579 A | 6/1999 |
| JP | 11221081 A | 8/1999 |
| JP | 2000270855 A | 10/2000 |
| JP | 200195598 A | 4/2001 |
| JP | 200379386 A | 3/2003 |
| JP | 2003235585 A | 8/2003 |
| JP | 2004275013 A | 10/2004 |
| JP | 2004275063 A | 10/2004 |
| WO | 9713872 A1 | 4/1997 |
| WO | 2004104203 A1 | 12/2004 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Guo et al., Protein tolerance to random amino acid change. PNAS., 2004, vol. 101 (25): 9205-9210.*
Seffernick et al., Melamine deaminase and Atrazine chlorohydrolase: 98 percent identical but functionally different. J. Bacteriol.,2001, vol. 183 (8): 2405-2410.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
Sakai, et al., "Purification and Properties of Fructosyl Lysine Oxidase from Fusarium oxysporum S-1F4", Kyoto University, vol. 59, pp. 487-491, (1995).
Sakaue, et al., "Thermostabilization of Bacterial Fructosyl-Amino Acid Oxidase by Directed Evolution", Applied and Environmental Microbiology, vol. 69, pp. 139-145, (2003).
Hirokawa, et al., "Molecular cloning and expression of the novel fructosyl peptide oxidases and their application for the measurement of glycated protein", Kikkoman Corporation, Biochemical and Biophysical Research Communications 311, pp. 104-111, (2003).
Yoshida, et al., "Primary structures of fungal fructosyl amino acid oxidases and their application to the measurement of glycated proteins", Eur. J. Biochem. 242, pp. 499-505, (1996).
Jeong, et al. The veA gene is necessary for the inducible expression by fructosyl amines of the *Aspergillus nidulans* faoA gene encoding fructosyl amino acid oxidase (amadoriase EC 1.5.3), Arch Microbiol 178, pp. 344-350, (2002).
Ferri, et al., Cloning and Expression of Fructosyl-amine Oxidase from Marine Yeast Pichia Species N1~1, Mar. Biotechnol. vol. 6, pp. 625-632, (2004).
Fujiwara, et al., "Alteration of substrate specificity of fructosyl-amino acid ozidase from Ulocladium sp. JS-103", J. BioSci. Bioeng., vol. 102, No. 3, pp. 241-243 (2006).

(Continued)

*Primary Examiner* — Ganapathirama Raghu
(74) *Attorney, Agent, or Firm* — Ping Wang; Andrews Kurth, LLP

(57) ABSTRACT

Disclosed are: a eukaryotic amadoriase which is prepared by introducing a mutation into DNA encoding a eukaryotic amadoriase derived from a microorganism belonging to the genus *Coniochaeta* or *Eupenicillium* so as to introduce a substitution into a specific amino acid residue in the eukaryotic amadoriase, thereby overcoming the defect associated with thermal stability; a gene or recombinant DNA for the eukaryotic amadoriase; and a process for production of a eukaryotic amadoriase having excellent thermal stability.

4 Claims, 2 Drawing Sheets

OTHER PUBLICATIONS

Hirokawa, et al., "Enzyme used for the determination of HbA1c", FEMS Micobiol. Lett., vol. 235, pp. 157-162 (2004).

Hirokawa, et al., "Distribution and properties of novel deglycating enzymes for fructosyl peptide in fungi", Arch. Microbiol., vol. 180, pp. 227-231 (2003).

Sakaue, et al., "Cloning and expression of fructosyl-amino acid oxidase gene from Corynebacterium sp. 2-4-1 in *Escherichia coli*", Biosci. Biotechnol. Biochem., vol. 66, No. 6, pp. 1256-1261 (2002).

International Search Report; Written Opinion of the International Searching Authority (International Application No. PCT/JP2007/058304), Jul. 24, 2007.

Kozo Hirokawa et al., "Enchancement of Thermostability of Fungal Deglycating Enzymes by Directed Evolution" Applied MIcrobiology and Biotechnology (2008) 78:775-781.

Supplementary European Search Report, Application No. EP 07741740, Jun. 20, 2010.

* cited by examiner

FIG. 1

```
Con. sp.          359  MCEHPKWKNFILATGDSHSFKILPNVGKHVVELIEGRLPEEMAYQWRWRPGG-DALKSRRAAPPKDLADMPGWKH------DP------       435
Eup. terrenum     359  ICEHPKWKNFILATGDSGHSFKLLPNIGKHVVELLEGSLSQEMAGAWRWRPGGD-ALRSRRGAPAKDLAEMPGWKHDAHL-------          437
Pyr. sp.          357  ICEHPQWKNFMLATGDSGHSFRKILPNIGKHVVELIEGTLAADLAHAWRWRPGIGDALQSRRAAPAKDLADMPGWNHDESPRAKL---         440
Art. sp.          360  ICEHPRWRNFILATGDSGHSFKLLPNIGKHVVELLEGRLADDLAQAWRWRPGQGDALKSRRAAPAKDLADMPGWNHDGDSGNATSGTSSE     449
Neo. vasinfecta   359  ICEHPRWKNFILATGDSGHSFKLLPTIGKHVVELVEGRLADDLAEAWRWRPGQGDARKSIRAAPAKDLADMPGWKHDQDSESR----        441
Pen. janthinellum 359  ICEHPKWKNFILATGDSGHSFKVLPNIGKHVVELIEGRLPQDLAGAWRWRPGGD-ALKSKRSAPAKDLAEMPGWKHDAKL-------         437
Asp. nidulans     359  VCEHPRWKGFYLATGDSGHSFKLLPNIGKHVVELLEERLESVFKDAWRWRPGSGDALKSRRAAPAKDLADMPGWRNEAK...             437
                       .**** *..*.************.**..********..*..  .*********..*.*.*.**.****.****.

Con. sp.          436  -KL   (SEQ ID NO:1)
Eup. terrenum     437  ---   (SEQ ID NO:2)
Pyr. sp.          440  ---   (SEQ ID NO:13)
Art. sp.          450  HKL   (SEQ ID NO:14)
Neo. vasinfecta   441  ---   (SEQ ID NO:15)
Pen. janthinellum 437  ---   (SEQ ID NO:16)
Asp. nidulans     437  ---   (SEQ ID NO:17)

Con. sp.          : Coniochaeta sp.
Eup. terrenum     : Eupenicillium terrenum
Pyr. sp.          : Pyrenochaeta sp.
Art. sp.          : Arthrinium sp.
Neo. vasinfecta   : Neocosmospora vasinfecta
Pen. janthinellum : Penicillium janthinellum
                    Asp. nidulans : Aspergillus nidulans
```

EUKARYOTIC AMADORIASE HAVING EXCELLENT THERMAL STABILITY, GENE AND RECOMBINANT DNA FOR THE EUKARYOTIC AMADORIASE, AND PROCESS FOR PRODUCTION OF EUKARYOTIC AMADORIASE HAVING EXCELLENT THERMAL STABILITY

FIELD

The present invention relates to eukaryotic amadoriases having excellent thermal stability; genes and recombinant DNAs for the eukaryotic amadoriases; and processes for production of eukaryotic amadoriases having excellent thermal stability.

BACKGROUND

An amadoriase oxidizes iminodiacetic acid or a derivative thereof (also referred to as "Amadori compound") in the presence of oxygen to catalyze a reaction to generate glyoxylic acid or α-ketoaldehyde, amino acid or peptide, and hydrogen peroxide.

Amadoriases have been found in bacteria, yeast, and fungi (e.g., see Patent Documents 1 to 4). Amadoriases have been purified from the genera *Aspergillus, Penicillium, Fusarium, Pichia, Coniochaeta, Eupenicillium, Pyrenochaeta, Arthriniuin, Neocosinospora, Corynebacterium* and *Agrobacterium* to determine the amino acid sequence of each amadoriase (e.g., see Non-Patent Documents 1 to 4 and Patent Documents 5 to 9).

These amadoriases can be classified into two types of prokaryotic and eukaryotic amadoriases. The prokaryotic amadoriases derived from procaryotes and the eukaryotic amadoriases derived from eucaryotes have amino acid sequences having high homologies with the amadoriases only in the same type, respectively, whereas the amino acid sequences have extremely low homologies between the different types of the eukaryotic and prokaryotic amadoriases.

The prokaryotic amadoriases had a problem of unfortunately losing their enzyme activities by separating some coenzymes during purification or storage of enzymes because of forming bonds with the coenzymes that are not covalent bonds. In contrast, the aforementioned problem confirmed in the prokaryotic amadoriases is not seen in the eukaryotic amadoriases because the eukaryotic amadoriases form covalent bonds with the coenzymes, and thus the eukaryotic amadoriases have excellent practical characteristics.

In the field of clinical diagnosis of diabetes mellitus, attention has been given to glycated hemoglobin (HbA1c) as a glycemic control marker significant for diagnosis of diabetic patients and control of conditions. For a method of quickly and simply measuring the HbA1c, there has been proposed an enzymic method using an amadoriase, that is, a method of measuring glycated amino acids or glycated peptides, released by decomposing the HbA1c by, e.g., protease (for example, see Patent Documents 10 to 13).

Thermal stability is demanded as an enzymatic property, where an amadoriase as an enzyme for clinical diagnosis of diabetes mellitus is formulated for a kit reagent. A eukaryotic amadoriase derived from a strain of *Aspergillus terreus* GP1 has exhibited a residual activity of about 40% in heat treatment at 45° C. for 10 minutes (for example, see Non-Patent Document 2). A eukaryotic amadoriase derived from a strain of *Fusarium oxysporum* S-1F4 has exhibited a residual activity of about 10% in heat treatment at 45° C. for 5 minutes (for example, see Non-Patent Document 5). A eukaryotic amadoriase derived from a strain of *Coniochaetidium savoryi* ATCC36547 has also exhibited a residual activity of 80% in heat treatment at equal to or less than 37° C. for 30 minutes (for example, see Patent Document 14). Furthermore, each of eukaryotic amadoriases derived from strains of *Arthrinium* sp. TO6, *Pyrenochaeta* sp. YH807, *Leptosphaeria nodorum* NBRC7480, *Pleospora herbarum* NBRC32012 and *Ophiobolus herpotrichus* NBRC6158 has exhibited a residual activity of 80% in heat treatment at equal to or less than 40° C. for 30 minutes. A eukaryotic amadoriase derived from a strain of *Neocosmospora vasinfecta* NBRC7590 has also exhibited a residual activity of 80% in heat treatment at equal to or less than 45° C. for 30 minutes. A eukaryotic amadoriase derived from a strain of *Curvularia clavata* YH923 has exhibited a residual activity of 80% in heat treatment at equal to or less than 50° C. for 30 minutes (for example, see Patent Document 14).

However, further thermal stability is needed where these eukaryotic amadoriases are used as enzymes for clinical diagnosis. That is, further higher thermal stability is demanded in consideration of formulation of the eukaryotic amadoriases, as enzymes for clinical diagnosis of diabetes mellitus, for a kit reagent, and use as enzyme sensors, although the enzyme derived from the strain of *Curvularia clavata* YH923, having the highest thermal stability, has exhibited a residual activity of 80% in heat treatment at equal to or less than 50° C. for 30 minutes.

For a general technique, there has been known a method of adding mutations to DNAs encoding enzymes, introducing substitutions into the amino acids of enzymes and selecting enzymes with excellent thermal stability in order to improve the thermal stability of the enzymes. In addition, if an example of improving thermal stability by amino acid substitution in enzymes with high homology has been already known, improvement in the thermal stability can be expected based on this information.

Indeed, in a prokaryotic amadoriase derived from *Corynebacterium* bacteria, the thermal stability of the prokaryotic amadoriase has been demonstrated to be improved by replacing several amino acids (for example, see Non-Patent Document 5), and thermal stability can be also introduced into other prokaryotic amadoriases.

However, since, as described above, the amino acid sequences of the amadoriases have extremely low homologies between the types of the eukaryotic amadoriase and the prokaryotic amadoriase, it was impossible to expect the improvement of the thermal stability of the eukaryotic amadoriase on the basis of information on amino acid mutations involved in the thermal stability of the prokaryotic amadoriase derived from *Corynebacterium* bacteria.

Also, there has been no report that the well-known eukaryotic amadoriase was improved in thermal stability by replacement of amino acids, and existing information on the thermal stability of the eukaryotic amadoriase can not be utilized. Extensive, specific researches are demanded for determining which amino acid to replace in a sequence in order to practically improve the eukaryotic amadoriase type in thermal stability.

Patent Document 1: Japanese Patent Publication No. 05-33997;
Patent Document 2: Japanese Patent Application Laid-Open Publication No. 2000-270855;
Patent Document 3: Japanese Patent Application Laid-Open Publication No. 07-289253;
Patent Document 4: Japanese Patent Application Laid-Open Publication No. 08-336386;

Patent Document 5: Japanese Patent Application Laid-Open Publication No. 2003-235585;

Patent Document 6: Japanese Patent Application Laid-Open Publication No. 2004-275063;

Patent Document 7: Pamphlet of WO 2004/104203;

Patent Document 8: Japanese Patent Application Laid-Open Publication No. 11-155579;

Patent Document 9: Japanese Patent Application Laid-Open Publication No. 2003-79386;

Patent Document 10: Japanese Patent Application Laid-Open Publication No. 2001-95598;

Patent Document 11: Bulletin of Japanese Patent Publication No. 05-33997;

Patent Document 12: Japanese Patent Application Laid-Open Publication No. 11-127895;

Patent Document 13: Pamphlet of WO 97/13872;

Patent Document 14: Japanese Patent Application Laid-Open Publication No. 2004-275013;

Non-Patent Document 1: Arch. Microbiol. 178, 344-50, 2002;

Non-Patent Document 2: Eur. J. Biochem. 242, 499-505, 1996;

Non-Patent Document 3: Mar. Biotechnol. 6, 625-32, 2004;

Non-Patent Document 4: Biosci. Biotechnol. Biochem. 59, 487-91, 1995;

Non-Patent Document 5: Appl. Environ. Microbiol. 69, 139-45, 2003.

DISCLOSURE OF INVENTION

The problem to be solved by the invention is to overcome the defects associated with thermal stability in a conventional eukaryotic amadoriase and to provide a eukaryotic amadoriase having excellent thermal stability for use as an enzyme for clinical diagnosis of diabetes or an enzyme sensor.

As a result of repeated extensive researches for solving the aforementioned problem, the present inventors accomplished the present invention in finding that the aforementioned problem can be solved by substituting a specific amino acid residue for a specific amino acid residue in a eukaryotic amadoriase (FPOX-CE) derived from the genus *Coniochaeta* or a eukaryotic amadoriase (FPOX-EE) derived from the genus *Eupenicillium*.

More specifically, the present invention is to provide the following inventions:

(1) A eukaryotic amadoriase having the following characteristics (a) and/or (b):
  (a) equal to or more than 83% residual activity in heat treatment at pH 8.0 and 50° C. for 30 minutes; and
  (b) having an amino acid sequence having equal to or more than 75% homology to the amino acid sequence of the eukaryotic amadoriase according to SEQ ID NO: 1.

(2) The eukaryotic amadoriase according to (1) described above, having one or more alterations or mutations of amino acids at positions corresponding to amino acids selected from the group consisting of the following (a) to (c):
  (a) glycine at position 184 in an amino acid sequence according to SEQ ID NO: 1 in the sequence listing;
  (b) asparagine at position 272 in an amino acid sequence according to SEQ ID NO: 1 in the sequence listing; and
  (c) histidine at position 388 in an amino acid sequence according to SEQ ID NO: 1 in the sequence listing.

(3) A eukaryotic amadoriase having the following characteristics (a) and (b):
  (a) equal to or more than 83% residual activity in heat treatment at 50° C. for 30 minutes; and
  (b) having an amino acid sequence shown in SEQ ID NO: 1 in the sequence listing, with one or several deletions, inserts, additions and/or substitutions of amino acids.

(4) A eukaryotic amadoriase having one or more alterations or mutations of an amino acid at a position corresponding to arginine at position 94, glycine at position 184, phenylalanine at position 265, asparagine at position 272, histidine at position 302 or histidine at position 388 in an amino acid sequence according to SEQ ID NO: 1 in the sequence listing.

(5) A eukaryotic amadoriase comprising, in an amino acid sequence according to SEQ ID NO: 1 in the sequence listing, combinations of one or more alterations or mutations selected from the group consisting of the following (a) to (f):
  (a) replacement of arginine at position 94 by lysine;
  (b) replacement of glycine at position 184 by aspartic acid;
  (c) replacement of phenylalanine at position 265 by leucine;
  (d) replacement of asparagine at position 272 by aspartic acid;
  (e) replacement of histidine at position 302 by arginine; and
  (f) replacement of histidine at position 388 by tyrosine.

(6) A eukaryotic amadoriase, wherein asparagine at position 272 is replaced by aspartic acid, histidine at position 302 is replaced by arginine, and histidine at position 388 is replaced by tyrosine in an amino acid sequence according to SEQ ID NO: 1 in the sequence listing.

(7) A eukaryotic amadoriase having the following characteristics (a) and/or (b):
  (a) equal to or more than 50% residual activity in heat treatment at pH 8.0 and 50° C. for 30 minutes; and
  (b) having an amino acid sequence having equal to or more than 75% homology to the amino acid sequence of the eukaryotic amadoriase according to SEQ ID NO: 2 in the sequence listing.

(8) A eukaryotic amadoriase having the following characteristics (a) and (b):
  (a) equal to or more than 50% residual activity in heat treatment at 50° C. for 30 minutes; and
  (b) having an amino acid sequence shown in SEQ ID NO: 2 in the sequence listing, with one or several deletions, inserts, additions and/or substitutions of amino acids.

(9) A eukaryotic amadoriase having one or more alterations or mutations of an amino acid at a position corresponding to glycine at position 184, asparagine at position 272 or histidine at position 388 in an amino acid sequence according to SEQ ID NO: 2 in the sequence listing.

(10) A eukaryotic amadoriase comprising, in an amino acid sequence according to SEQ ID NO: 2 in the sequence listing, combinations of one or more alterations or mutations selected from the group consisting of the following (a) to (c):
  (a) replacement of glycine at position 184 by aspartic acid;
  (b) replacement of asparagine at position 272 by aspartic acid; and
  (c) replacement of histidine at position 388 by tyrosine.

(11) A eukaryotic amadoriase, wherein glycine at position 184 is replaced by aspartic acid, asparagine at position 272 is replaced by aspartic acid, and histidine at position 388 is replaced by tyrosine in an amino acid sequence according to SEQ ID NO: 2 in the sequence listing.

(12) A eukaryotic amadoriase gene encoding the amino acid sequence according to any one of (1) to (11) described above.

(13) A recombinant vector comprising the eukaryotic amadoriase gene according to (12) described above.

(14) A host cell comprising the recombinant vector according to (13) described above.

(15) A method of generating a eukaryotic amadoriase, comprising the following steps of:
(a) culturing the host cell according to (14) described above;
(b) expressing a eukaryotic amadoriase gene included in the host cell; and
(c) isolating the eukaryotic amadoriase from a culture.

(16) A kit for use in measurement of glycated protein, comprising the eukaryotic amadoriase according to any of (1) to (11) described above.

(17) A kit for use in measurement of glycated hemoglobin, comprising the eukaryotic amadoriase according to any of (1) to (11) described above.

(18) A eukaryotic amadoriase having the following physicochemical properties (a) to (f):
(a) function and substrate specificity: acting on fructosyl valyl histidine in the presence of oxygen and catalyzing a reaction to generate α-ketoaldehyde, valyl histidine, and hydrogen peroxide;
(b) optimum pH: pH 6.0 to 8.0;
(c) range of temperatures good for function: 20 to 45° C.,
(d) thermal stability, equal to or more than 83% residual activity in heat treatment at pH 8.0 and 50° C. for 30 minutes;
(e) range of stable pH: pH 6.0 to 9.0; and
(f) molecular weight: about 52,000 (SDS-PAGE).

According to the present invention, a eukaryotic amadoriase with excellent thermal stability and a gene encoding the eukaryotic amadoriase is provided, and advantageously utilized as an enzyme for diagnosis of diabetes mellitus and a kit for measurement of a diabetes mellitus marker.

BRIEF DESCRIPTION OF THE DRAWING

FIG. 1 is a view of alignment of a eukaryotic amadoriase sequence including an amino acid sequence (first line) shown in SEQ ID NO: 1 and an amino acid sequence having equal to or more than 75% homology to the amino acid sequence.

BEST MODE FOR CARRYING OUT THE INVENTION

The present invention is described in detail below.

An amadoriase, which is also referred to as fructosyl amino acid oxidase and fructosyl amine oxidase, refers to an enzyme that oxidizes iminodiacetic acid or a derivative thereof (Amadori compound) in the presence of oxygen to catalyze a reaction to generate glyoxylic acid or α-ketoaldehyde, amino acid or peptide, and hydrogen peroxide.

Amadoriases are widely distributed over the natural world and can be obtained by searching for enzymes derived from microorganisms, animals or vegetables. In the microorganisms, amadoriases can be obtained from, for example, filamentous fungi, yeast or bacteria.

A eukaryotic amadoriase according to the present invention is an altered eukaryotic amadoriase excellent in thermal stability, produced based on a eukaryotic amadoriase (FPOX-CE or FPOX-EE) derived from the genus *Coniochaeta* having an amino acid sequence shown in SEQ ID NO: 1 or the genus *Eupenicillium* having an amino acid sequence shown in SEQ ID NO: 2. Examples of such mutants may include, for example, a eukaryotic amadoriase having an amino acid sequence having a high homology (for example, 75% or higher, preferably 85% or higher, more preferably 95% or higher) with SEQ ID NO: 1 or 2 and a eukaryotic amadoriase having the amino acid sequence of SEQ ID NO: 1 or 2, in which one or several amino acids are altered or mutated, or deleted, replaced, added and/or inserted. It is noted that, where conditions on thermal stability and/or an amino acid sequence described in claims are met, such a mutant may be also produced based on a eukaryotic amadoriase derived from another filamentous fungus or yeast, such as the genus *Eupenicillium, Pyrenochaeta, Arthrinium, Curvlaria, Neocosmospora, Penicillium, Fusarium* or *Aspergillus*.

A gene cloning method that is generally used is typically used for obtaining genes in accordance with the present invention encoding these eukaryotic amadoriases (hereinafter, also referred to as merely "eukaryotic amadoriase gene"). For example, chromosomal DNA or mRNA can be extracted from a microorganism fungus body or various cells having an ability to produce a eukaryotic amadoriase by a usual method, such as a method described in "Current Protocols in Molecular Biology" (WILEY Interscience, 1989). In addition, cDNA can be synthesized using mRNA as a template. A chromosomal DNA or cDNA library can be made using the chromosomal DNA or cDNA obtained in such a manner.

DNA including the full length of a target eukaryotic amadoriase gene can be then obtained by a method of synthesizing an appropriate probe DNA on the basis of the amino acid sequence of the aforementioned eukaryotic amadoriase and selecting eukaryotic amadoriase genes from the chromosomal DNA or cDNA library using the probe DNA, or by producing an appropriate primer DNA on the basis of the aforementioned amino acid sequence, amplifying DNA including target gene segments encoding a eukaryotic amadoriase by an appropriate polymerase chain reaction (PCR), such as 5' RACE method or 3' RACE method, and linking these DNA fragments.

Preferred examples of genes encoding eukaryotic amadoriases obtained in such a manner include an example of a eukaryotic amadoriase gene derived from the genus *Coniochaeta* (Patent Document 5).

These eukaryotic amadoriase genes are preferably linked to various vectors according to a usual method in terms of handling. For example, DNA encoding a eukaryotic amadoriase gene can be extracted and purified from a recombinant plasmid pKK223-3-CFP (Patent Document 5) including DNA encoding a eukaryotic amadoriase gene derived from a strain of *Coniochaeta* sp. NISL9330 by using QIAGEN (manufactured by Qiagen K.K.).

In addition, vectors that can be used in the present invention are not limited to the aforementioned plasmid but include, for example, any other vector well known to those skilled in the art, such as bacteriophage or cosmid. Specifically, for example, pBluescriptII SK+ (manufactured by STRATAGENE Corporation) is preferred.

Mutation treatment of a eukaryotic amadoriase gene may be effected by any well-known method depending on intended mutation form. More specifically, a method of making a chemical to be a mutagen contact with and act on a eukaryotic amadoriase gene or recombinant DNA integrated with the gene; an ultraviolet irradiation method; a genetic engineering technique; or a method of making full use of a protein engineering technique can be widely used.

Chemicals to be mutagens used in the aforementioned mutation treatment may include, for example, hydroxylamine, N-methyl-N'-nitro-N-nitrosoguanidine, nitrous acid, sulfurous acid, hydrazine, formic acid, or 5-bromouracil.

Various conditions for the contact/function, which may be adopted, include conditions depending on the type of a drug to be used and are not particularly limited where a desired mutation can be actually induced in a eukaryotic amadoriase gene. Usually, the desired mutation can be induced by contact/function under a reaction temperature of 20 to 80° C. for 10 minutes or longer, preferably 10 to 180 minutes, preferably at the aforementioned drug concentration of 0.5 to 12 M. The ultraviolet irradiation may be also performed according to a usual method as described above (Gendai Kagaku, pp. 24-30, the June 1989 issue).

As the method of making full use of the protein engineering technique, a technique known as site-specific mutagenesis can be generally used, and examples of which include a Kramer method (Nucleic Acids Res., 12, 9441 (1984): Methods Enzymol., 154, 350 (1987): Gene, 37, 73 (1985)), an Eckstein method (Nucleic Acids Res., 13, 8749 (1985): Nucleic Acids Res., 13, 8765 (1985): Nucleic Acids Res, 14, 9679 (1986)), and a Kunkel method (Proc. Natl. Acid. Sci. U.S.A., 82, 488 (1985): Methods Enzymol., 154, 367 (1987)).

A technique known as general polymerase chain reaction can be also used (Technique, 1, 11 (1989)). In addition to the aforementioned genetic alteration method, by an organic synthesis method or synthetic method of an enzyme, desired altered eukaryotic amadoriase genes can be also directly synthesized.

The DNA base sequences of eukaryotic amadoriase genes obtained by the aforementioned methods may be determined or verified by, for example, using a multi-capillary DNA analysis system CEQ 2000 (manufactured by Beckman Coulter, Inc.).

Eukaryotic amadoriase genes obtained as described above are integrated into a vector such as a bacteriophage, a cosmid, or a plasmid used in transformation of a procaryotic or eucaryotic cell by a usual method, and a host corresponding to each vector can be transformed or transduced by a usual method. For example, as the host, a microorganism belonging to the genus *Escherichia*, for example, obtained recombinant DNA is used to transform or be transduced into a strain of *E. coli* K-12, preferably a strain of *E. coli* JM109 or *E. coli* DH5α or the like (each of which are manufactured by Takara Bio Inc.) to obtain each strain.

Subsequently, for example, a following method may be used for selecting producing strains of a eukaryotic amadoriase according to the present invention.

First, several replicas are collected with sterilized velvet cloths, from LB agar media, in which the aforementioned obtained transformants form colonies, to new agar media, and the media are cultured. When the sizes of the colonies in the replicated agar media are adequate, membranes immersed into a bacteriolytic agent such as lysozyme are put on the media, and the media are left at rest at 37° C. for about 1 hour to effect bacteriolysis. In this step, the membranes adsorb bacteriolyzed crude enzyme solution.

The membranes adsorbing the crude enzyme solution are left at rest under the condition of 55° C. for 1 hour and thereafter put on membranes immersed into a 0.1 M potassium phosphate buffer solution (pH 8.0) including fructosyl valine, peroxidase, TOOS and 4-amino antipyrine as a substrate to observe a purple coloring degree. A coloring test on the producing strains of the pre-altered eukaryotic amadoriases is also conducted by a similar process to select target transformants by comparison of the producing strains.

In such a manner, a transformant having an ability to produce a eukaryotic amadoriase according to the present invention having excellent thermal stability can be obtained.

Furthermore, as necessary, an altered eukaryotic amadoriase that is further excellent in thermal stability and a transformant having an ability to produce the eukaryotic amadoriase can be also obtained by further repeatedly introducing mutations into the altered eukaryotic amadoriase genes by the alteration method described above using a transformant having an ability to produce a eukaryotic amadoriase with thermal stability.

Examples of transformants producing eukaryotic amadoriases excellent in thermal stability as obtained in such a manner may include a strain of *E. coli* JM109 (pKK223-3-CFP-T7) producing eukaryotic amadoriases with a percent residual activity of 83% or more, preferably 90% or more, more preferably 95% or more, by heat treatment at pH 8.0 and 50° C. for 30 minutes. The plasmid pKK223-3-CFP-T7 including a gene encoding a eukaryotic amadoriase according to the present invention described as an example was deposited at the Independent Administrative Agency, National Institute of Advanced Industrial Science and Technology, International Patent Organism Depository, in Central 6, 1, Higashi 1-chome, Tsukuba-shi, Ibaraki-ken, Japan, on Mar. 31, 2006, and was given Deposit No. FERM BP-10593.

The homology of an amino acid sequence may be calculated by a program such as maximum matching or search homology of GENETYX-Mac (manufactured by Software Development Co., Ltd.), or a program such as maximum matching or multiple alignment of DNASIS Pro (manufactured by Hitachi Software Engineering Co., Ltd.).

A method of identifying "position corresponding to an amino acid" may be also performed by comparing amino acid sequences using a well-known algorithm such as a Lipman-Pearson method to assign maximum homology to conserved amino acid residues present in the amino acid sequence of each eukaryotic amadoriase. The positions of the homologous amino acid residues in each of the eukaryotic amadoriase sequences can be determined regardless of insertion or deletion of amino acid residue(s) in the amino acid sequences by aligning the amino acid sequences of the eukaryotic amadoriases by such a method. Conceivably, the homologous amino acid residues are located at the same positions in three-dimensional structures, and the target eukaryotic amadoriases can be estimated to have similar effect in terms of specificity functions.

Figure 1:
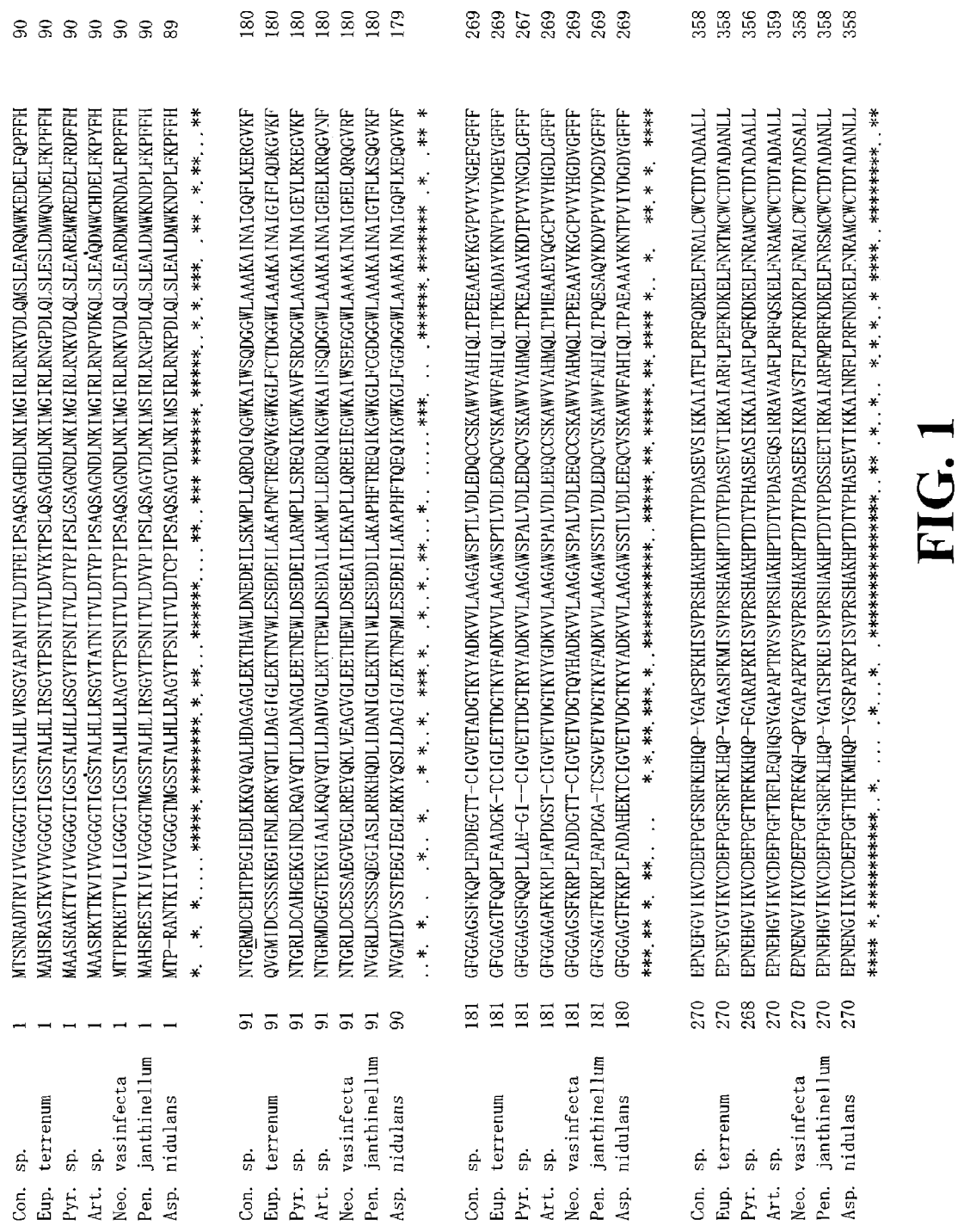

As used herein, "position corresponding to glycine at position 184 in amino acid sequence according to SEQ ID NO: 1" means an amino acid corresponding to glycine at position 184 in the eukaryotic amadoriase of SEQ ID NO: 1 when the amino acid sequence of the identified eukaryotic amadoriases are compared with the amino acid sequences of the eukaryotic amadoriases derived from the genus *Coniochaeta* shown in SEQ ID NO: 1. Thereby, the amino acid may be identified referring to FIG. 1, in which amino acid sequences are aligned by the aforementioned method of identifying "amino acid residue at corresponding position".

More specifically, the amino acid corresponds to glycine at position 184 in the eukaryotic amadoriase derived from the genus *Eupenicillium*, glycine at position 184 in the eukaryotic amadoriase derived from the genus *Pyrenochaeta*, glycine at position 184 in the eukaryotic amadoriase derived from the genus *Arthrinium*, glycine at position 184 in the eukaryotic amadoriase derived from the genus *Neocosmospora*, serine at position 184 in the eukaryotic amadoriase derived from the genus *Penicillium*, or glycine at position 183 in the eukaryotic amadoriase derived from the genus *Aspergillus*.

"Position corresponding to asparagine at position 272 in amino acid sequence according to SEQ ID NO: 1" means an amino acid corresponding to asparagine at position 272 in an amino acid sequence according to SEQ ID NO: 1 when the amino acid sequence of the identified eukaryotic amadoriases are compared with the amino acid sequences of the eukaryotic amadoriases derived from the genus *Coniochaeta* shown in SEQ ID NO: 1. The amino acid may be also identified referring to FIG. 1, in which amino acid sequences are aligned by the aforementioned method.

More specifically, the amino acid corresponds to asparagine at position 272 in the eukaryotic amadoriase derived from the genus *Eupenicillium*, asparagine at position 270 in the eukaryotic amadoriase derived from the genus *Pyrenochaeta*, asparagine at position 272 in the eukaryotic amadoriase derived from the genus *Arthrinium*, asparagine at position 272 in the eukaryotic amadoriase derived from the genus *Neocosmospora*, asparagine at position 272 in the eukaryotic amadoriase derived from the genus *Penicillium*, or asparagine at position 272 in the eukaryotic amadoriase derived from the genus *Aspergillus*.

Furthermore, "position corresponding to histidine at position 388 in amino acid sequence according to SEQ ID NO: 1" means an amino acid corresponding to histidine at position 388 in the eukaryotic amadoriase according to SEQ ID NO: 1 when the amino acid sequence of the identified eukaryotic amadoriases are compared with the amino acid sequences of the eukaryotic amadoriases derived from the genus *Coniochaeta* shown in SEQ ID NO: 1. The amino acid may be also identified referring to FIG. 1, in which amino acid sequences are aligned by the aforementioned method.

More specifically, the amino acid corresponds to histidine at position 388 in the eukaryotic amadoriase derived from the genus *Eupenicillium*, histidine at position 386 in the eukaryotic amadoriase derived from the genus *Pyrenochaeta*, histidine at position 389 in the eukaryotic amadoriase derived from the genus *Arthrinium*, histidine at position 388 in the eukaryotic amadoriase derived from the genus *Neocosmospora*, histidine at position 388 in the eukaryotic amadoriase derived from the genus *Penicillium*, or histidine at position 388 in the eukaryotic amadoriase derived from the genus *Aspergillus*.

In order to use a strain having an ability to produce a eukaryotic amadoriase excellent in thermal stability obtained as described above to produce the eukaryotic amadoriase, the strain may be cultured by a usual solid culture method, preferably by the adoption of a liquid culture method wherever possible.

In addition, as media to culture the aforementioned strains include, for example, media, in which one or more of inorganic salts such as sodium chloride, monopotassium phosphate, dipotassium phosphate, magnesium sulfate, magnesium chloride, ferric chloride, ferric sulfate and manganic sulfate are added to one or more nitrogen sources such as a yeast extract, trypton, peptone, a meat extract, a corn steep liquor and a leaching solution of soybean or wheat bran, and in addition, as needed, saccharine materials and vitamins and the like are appropriately added thereto, are used.

It is noted that it is appropriate to adjust the initial pH of the media to pH 7 to 9.

In addition, the culture is preferably performed at a culture temperature of 20 to 42° C., preferably a culture temperature of about 37° C. for 4 to 24 hours, further preferably at a culture temperature of about 37° C. for 4 to 8 hours, by aeration spinner submerged culture, shake culture or stationary culture.

Following termination of the culture, eukaryotic amadoriases may be collected from the cultures with generally employed enzyme collecting means. For example, a fungus body may be subjected to, for example, ultrasonic disintegration treatment or grinding treatment by a usual method; this enzyme may be extracted using a lytic enzyme such as lysozyme; or bacteriolysis may be effected on shaking or still standing in the presence of toluene to exhaust this enzyme from the fungus body to the outside. This solution is then filtrated or centrifuged to remove a solid content, and, as needed, removal of nucleic acid is performed with streptomycin sulfate, protamine sulfate or manganese sulfate and the like, followed by adding ammonium sulfate, alcohol or acetone to the solution to fractionate the solution and collecting sediments to obtain the crude enzymes of the eukaryotic amadoriases.

For further obtaining a eukaryotic amadoriase purified enzyme preparation from the crude enzyme of the aforementioned eukaryotic amadoriase, the purified eukaryotic amadoriase enzyme preparation can be obtained by a method appropriately selected from gel filtration methods using Sephadex, Ultrogel, Bio-Gel, etc.; adsorption-elution methods using ion exchangers; electrophoretic methods using polyacrylamide gels, etc.; adsorption-elution methods using hydroxyapatite; sedimentation methods such as sucrose density-gradient centrifugation; affinity chromatographic methods; and fractionation methods using a molecular sieve membrane, a hollow-fiber membrane, etc., or by a combination thereof. In such a manner, a desired eukaryotic amadoriase excellent in thermal stability can be obtained.

As used herein, "excellent in thermal stability" also refers to percent residual activity of 83% or more, preferably 90% or more, more preferably 95% or more, with respect to activity prior to heat treatment, following the heat treatment at pH 8.0 and 50° C. for 30 minutes for the eukaryotic amadoriases of SEQ ID NO: 1, and refers to percent residual activity of 50% or more, preferably 70% or more, with respect to activity prior to heat treatment, following the heat treatment at pH 8.0 and 50° C. for 30 minutes for the eukaryotic amadoriases of SEQ ID NO: 2, under reaction conditions in accordance with an activity measuring method and a thermal stability measuring method, which are described below. The eukaryotic amadoriase excellent in thermal stability significantly improves the keeping quality of products containing the enzyme and therefore is extremely industrially advantageous.

It is noted that the eukaryotic amadoriase excellent in thermal stability has a highly stabilized protein structure in itself, and thus, for example, is improved in resistance to protein protease.

When decomposition of HbA1c is performed with protease, followed by function of amadoriase, for measurement of HbA1c by the amadoriase, use of the amadoriase with high resistance to protease is extremely valuable. This is because, in this system of measurement, the protease affects not only HbA1c but also amadoriase to adversely affect the measured values of HbA1c. The use of the amadoriase having resistance to protease prevents decomposition of the amadoriase by the protease, eliminates the need for separation operation, and enables more accurate measurement. Protease treatment at high concentration, which has been previously impossible, is also enabled to improve the precision of measurement values. The time of protease reaction can be also shortened to lead to prompt measurement of HbA1c.

As used herein, "having resistance to protease" also refers to percent residual activity of 40% or more, preferably 60% or more, more preferably 80% or more, with respect to activity prior to protease treatment, following the 50 mU protease treatment at pH 8.0 and 37° C. for 30 minutes for the eukaryotic amadoriases. For example, in a method of measuring resistance to protease, the resistance to protease can be assessed by diluting an amadoriase enzyme solution or a crude enzyme solution with a 0.1 M phosphate buffer (pH 8.0) so that an amadoriase activity is about 0.05 U/ml, adding a 50 mU neutral protease (manufactured by Roche Corp.) to each sample, thereafter warming the sample at 37° C. for 30 minutes, measuring the activities of enzymes included in the samples prior to and following the neutral protease treatment, and determining percent remaining activities.

As a method of measuring the activity of a eukaryotic amadoriase, a method of measuring substrate affinity, and a method of measuring thermal stability, various methods can be used. As examples, the method of measuring the activity of a eukaryotic amadoriase and the method of measuring thermal stability, as used herein, are described below.

Method of Measuring Activity of Eukaryotic Amadoriase

Methods of measuring the enzyme activity of a eukaryotic amadoriase in accordance with the present invention include a method of measuring the amount of hydrogen peroxide generated by enzyme reaction and a method of measuring the amount of oxygen consumed in enzyme reaction as principal measuring methods. As an example, the method of measuring the amount of hydrogen peroxide is presented below.

For measurement of the activity of the eukaryotic amadoriase in accordance with the present invention, unless otherwise specified, fructosyl valine is used as a substrate. It is noted that, for enzyme titer, an enzyme level to generate 1 µmol of hydrogen peroxide per minute when being measured with fructosyl valine as a substrate was defined as 1 U.

Glycated amino acids such as fructosyl valine and glycated peptides such as fructosyl valyl histidine were synthesized and purified based on a method by Sakagami et al. (see a Japanese Patent Application Laid-Open Publication No. 2001-95598).

A. Preparation of Reagent
(1) Reagent 1: POD-4-AA Solution
1. In a 0.1 M potassium phosphate buffer solution (pH 8.0), 0 kU peroxidase (manufactured by Kikkoman Corporation) and 100 mg of 4-amino antipyrine (manufactured by Tokyo Chemical Industry Co., Ltd.) are dissolved to quantitatively determine the solution to 1 L.
(2) Reagent 2: TOOS Solution
In ion-exchange water, 500 mg of TOOS (manufactured by Dojindo Laboratories) was dissolved to quantitatively determine the solution to 100 ml.
(3) Reagent 3: Substrate Solution (150 mM; Final Concentration of 5 mM)
In ion-exchange water, 417 mg of fructosyl valine was dissolved to quantitatively determine the solution to 10 ml.

B. Measuring Method
Immixture of 2.7 ml of reagent 1, 1,100 µl of reagent 2 and 100 µl of enzyme solution was performed to preliminarily warm the mixture at 37° C. for 5 minutes. Subsequently, addition of 100 µl of reagent 3 was performed to well mix the mixture, followed by measuring its absorbance at 555 nm by a spectrophotometer (U-2000A, manufactured by Hitachi Ltd.). The measurement values were based on a variation in absorbance per minute from 1 to 3 minutes at 555 nm. A control solution was made by the same method except that 100 µl of ion-exchange water as a substitute for 100 µl of the reagent 3 was added. A graph, in which relationships with the amounts of generated coloring matters were examined, was prepared using a standard solution of hydrogen peroxide made beforehand as a substitute for the reagent 3 and ion-exchange water as a substitute for the enzyme solution. The number of micromoles of hydrogen peroxide generated per minute at 37° C. was calculated using the graph, and the unit of activity in the enzyme solution was based on the calculated value.

Method of Measuring Thermal Stability
A eukaryotic amadoriase crude enzyme solution or a eukaryotic amadoriase purified preparation was diluted with a 0.1 M phosphate buffer (pH 8.0) including 10% xylitol so as to be about 0.1 U/ml, and the diluted solution was warmed at 50° C. for 30 minutes. The enzyme activities of the samples prior to and following heating were measured to determine a remaining (enzyme) activity (%) to assess the stability.

The present invention is further specifically described below referring to examples, but the technical scope of the present invention is not limited at all by these examples.

EXAMPLE 1

(1) Preparation of Recombinant Plasmid pKK223-3-CFP DNA

A strain of E. coli JM109 (pKK223-3-CFP) having the recombinant plasmid of a eukaryotic amadoriase (SEQ ID NO: 1) gene derived from the genus Coniochaeta (Patent Document 5, FERM BP-8132, deposited at the Independent Administrative Agency, National Institute of Advanced Industrial Science and Technology, International Patent Organism Depository, in Chuou 6, 1, Higashi 1-chome, Tsukuba-shi, Ibaraki-ken, Japan, on Aug. 1, 2002) was inoculated into 100 ml of LB-amp medium [1% (W/V) Bactotrypton, 0.5% (W/V) Peptone, 0.5% (W/V) NaCl, 50 µg/ml Ampicilin] and the medium was shake-cultured at 37° C. for 20 hours to obtain cultures.

Harvest was performed to obtain a fungus body by centrifuging the cultures at 7,000 rpm for 5 minutes. A recombinant plasmid pKK223-3-CFP was extracted and purified from the fungus body using QIAGEN tip-100 (manufactured by Qiagen K.K.) to obtain 100 µg of recombinant plasmid pKK223-3-CFP DNA.

EXAMPLE 2

(2) Alteration Operation of Recombinant Plasmid pKK223-3-CFP DNA

Using 20 µg of 100 µg of the aforementioned recombinant plasmid pKK223-3-CFP DNA, XL1-RED (manufactured by Stratagene Ltd.) (prone to cause replication error of plasmid and alteration in case of growth) was transformed according to the method of D. M. Morrison (Method in Enzymology, 68, 326-331, 1979) to obtain about 5,000 transformants.

To collect plasmid DNA from all colonies, QIAGEN sol I (manufactured by Qiagen K.K.) was added to an agar medium, the colonies were scraped up together with QIAGEN sol I by a spreader, the solution was collected with Pipetman, and thereafter 100 µg of recombinant plasmid pKK223-3-CFP DNA subjected to an alteration operation was obtained by a usual plasmid collecting method. Using 20 µg of the aforementioned altered recombinant plasmid pKK223-3-CFP DNA, strains of E. coli JM109 were transformed according to the method of D. M. Morrison (Method in Enzymology, 68, 326-331, 1979) to obtain about 1,000 transformants possessing the altered plasmid.

EXAMPLE 3

(3) Searching of Eukaryotic Amadoriase Excellent in Thermal Stability

First, all of the aforementioned obtained transformants were replicated on new LB-amp agar media using velvet cloths. The colonies on the replica plates were transferred to Hybond-N+ (manufactured by Amersham Corporation), and this Hybond-N+ was immersed into 10 mg/ml of solution of lysozyme (manufactured by Sigma Co.). When this Hybond-N+ was treated at 48° C. for 1 hour and thereafter immersed into a 0.1 M potassium phosphate buffer solution (pH 8.0) including 2 mM fructosyl valine, 1 mg/ml of peroxidase (manufactured by Kikkoman Corporation), 1 mg/ml of 4-amino antipyrine (manufactured by Tokyo Chemical Industry Co., Ltd.) and 10 mg/ml of TOOS (manufactured by Dojindo Laboratories), a few strains exhibiting strong coloring were observed.

The colonies corresponding to the strong coloring were selected on the master plates, and altered eukaryotic amadoriases encoded by plasmid were produced by liquid culture in 2 ml of LB-amp medium.

Following the culture, each obtained fungus body was washed with a 0.1 M potassium phosphate buffer solution (pH 8.0), ultrasonically broken, and centrifuged at 15,000 rpm for 10 minutes to prepare 1.5 ml of each crude enzyme solution. The solutions were ultrasonically broken and centrifuged at 12,000 rpm for 5 minutes, and then supernatants were collected. Using the crude enzyme solutions, remaining activities (%) (activity following treatment/activity prior to treatment) were calculated according to the aforementioned method (method of measuring thermal stability) of measuring thermal stability.

Two altered eukaryotic amadoriases improved in percent residual activity and producing $E.$ $coli$ thereof could be obtained by similar culture, extraction and heat treatment, and comparing with the percent remaining activities of eukaryotic amadoriases prior to the alteration, of which the activities were measured.

The two obtained strains were shake-cultured in 2 ml of LB-amp media at 37° C. for 18 hours, and plasmids were isolated from the culture media using GFX Micro Plasmid Prep Kit (manufactured by Amersham Corporation). The plasmids were named pKK223-3-CFP-T1 and pKK223-3-CFP-T2, respectively, and a DNA base sequence encoding a eukaryotic amadoriase in each plasmid was determined using a multi-capillary DNA analysis system CEQ 2000 (manufactured by Beckman Coulter, Inc.).

As a result, mutations, in which histidine at position 302 in an amino acid sequence according to SEQ ID NO: 1 was replaced by arginine in pKK223-3-CFP-T1 and histidine at position 388 in an amino acid sequence according to SEQ ID NO: 1 was replaced by tyrosine in pKK223-3-CFP-T2, were found to be introduced.

EXAMPLE 4

(4) Production of Double Mutant pKK223-3-CFP-T3

The recombinant plasmids pKK223-3-CFP-T1 and pKK223-3-CFP-T2 were double-digested with restriction enzymes AatII and SacI. By agarose gel electrophoresis, about 1 kb DNA fragment and about 5 kb DNA fragment were dispensed from the aforementioned pKK223-3-CFP-T1 DNA and pKK223-3-CFP-T2 DNA, respectively, and purified by a usual method. Furthermore, both DNA fragments were linked using T4 DNA ligase, and the strains of $E.$ $coli$ JM109 were transformed to obtain a recombinant plasmid pKK223-3-CFP-T3.

The strains of $E.$ $coli$ JM109 (pKK223-3-CFP-T1), $E.$ $coli$ JM109 (pKK223-3-CFP-T2) and $E.$ $coli$ JM109 (PKK223-3-CFP-T3) possessing each recombinant plasmid obtained in such a manner were cultured in LB-amp media at 37° C. for 20 hours. Subsequently, each fungus body was washed with a 0.1 M potassium phosphate buffer solution at pH 8.0, ultrasonically broken, and centrifuged at 15,000 rpm for 10 minutes to prepare 1.5 ml of each crude enzyme solution.

For the enzyme solutions prepared in such a manner, the enzyme activities of remaining amadoriase were measured by the aforementioned method (method of measuring thermal stability). The results are shown in Table 1.

In Table 1, pKK223-3-CFP represents a wild-type eukaryotic amadoriase derived from the strain of $E.$ $coli$ JM109 (pKK223-3-CFP), and the other three enzymes represent the eukaryotic amadoriases of the present invention. As is apparent from this Table 1, the eukaryotic amadoriases obtained in the present invention are found to have excellent thermal stability.

TABLE 1

| Plasmid | Mutation | Residual Activity (%) |
| --- | --- | --- |
| pKK223-3-CFP | — | 30.4 |
| pKK223-3-CFP-T1 | H302R | 58.1 |
| pKK223-3-CFP-T2 | H388Y | 65.4 |
| pKK223-3-CFP-T3 | H302R, H388Y | 83.2 |

EXAMPLE 5

(5) Accumulation of Alteration

Plasmid DNA was prepared from the strain of $E.$ $coli$ JM109 (pKK223-3-CFP-T3) as an altered eukaryotic amadoriase producing strain, obtained in the aforementioned (4), by the method as described in the aforementioned (1). In addition, a mutation was introduced by the method in the aforementioned (2), and subsequently the method in the aforementioned (3) was used to perform selection with the previously obtained altered eukaryotic amadoriases as comparative controls in this example 5. Four strains of $E.$ $coli$ producing eukaryotic amadoriases, which had high percent remaining activities in heat treatment at pH 8.0 and 50° C. for 30 minutes and were further altered, were obtained. Shake culture was performed in 2 ml of LB-amp media at 37° C. for 18 hours using the four strains of $E.$ $coli$ obtained in such a manner.

Plasmids were isolated from the culture media using GFX Micro Plasmid Prep Kit (manufactured by Amersham Corporation). The plasmids were named pKK223-3-CFP-T4, pKK223-3-CFP-T5, pKK223-3-CFP-T6 and pKK223-3-CFP-T7, respectively, and a DNA base sequence encoding a eukaryotic amadoriase in each plasmid was determined using a multi-capillary DNA analysis system CEQ 2000 (manufactured by Beckman Coulter, Inc.).

As a result, in addition to mutations, in which histidine at position 302 was replaced by arginine and histidine at position 388 was replaced by tyrosine, mutations, in which arginine at position 94 was replaced by lysine in pKK223-3-CFP-T4, glycine at position 184 by aspartic acid in pKK223-3-CFP-T5, phenylalanine at position 265 by leucine in pKK223-3-CFP-T6, and asparagine at position 272 by aspartic acid in pKK223-3-CFP-T7, were found to be introduced.

The strains of $E.$ $coli$ JM109 (pKK223-3-CFP-T4), $E.$ $coli$ JM109 (pKK223-3-CFP-T5), $E.$ $coli$ JM109 (pKK223-3-CFP-T6) and $E.$ $coli$ JM109 (PKK223-3-CFP-T7) possessing the recombinant plasmids obtained in such a manner were cultured in LB-amp media at 37° C. for 20 hours, and each fungus body was washed with a 0.1 M potassium phosphate buffer solution (pH 8.0), thereafter ultrasonically broken, and centrifuged at 15,000 rpm for 10 minutes to prepare 1.5 ml of each crude enzyme solution.

For the enzyme solutions prepared in such a manner, the remaining enzyme activities were measured by the aforementioned method (method of measuring thermal stability). The results are shown in Table 2.

In Table 2, pKK223-3-CFP represents the eukaryotic amadoriase derived from the strain of $E.$ $coli$ JM109 (pKK223-3-CFP) prior to the alteration, and the other five enzymes represent the eukaryotic amadoriases of the present invention. As is apparent from this Table 2, the eukaryotic amadoriases obtained in the present invention are found to have the activities that are barely lost even by heat treatment at pH 8.0 and 50° C. for 30 minutes and to have excellent thermal stability.

TABLE 2

| Plasmid | Mutation | Residual Activity (%) |
|---|---|---|
| pKK223-3-CFP | — | 30.4 |
| pKK223-3-CFP-T3 | H302R, H388Y | 83.2 |
| pKK223-3-CFP-T4 | H302R, H388Y, R94K | 94.6 |
| pKK223-3-CFP-T5 | H302R, H388Y, G184D | 99.5 |
| pKK223-3-CFP-T6 | H302R, H388Y, F265L | 100.0 |
| pKK223-3-CFP-T7 | H302R, H388Y, N272D | 96.5 |

EXAMPLE 6

(6) Production and Purification of Eukaryotic Amadoriase of the Present Invention The transformants, *E. coli* JM109 pKK223-3-CFP-T7), producing the eukaryotic amadoriase of the present invention, obtained as described above, were inoculated into 10 L of LB-amp medium, and spinner-cultured at a culture temperature of 30° C. for 24 hours on the conditions of an airflow rate of 1 L/min and a stirring rate of 600 rpm using a jar fermentor.

Harvest of the fungi was performed by centrifuging 10 L of the obtained culture medium at 7,000 rpm for 10 minutes, and the fungi were suspended into 500 ml of buffer A (10 mM phosphoric acid buffer, 1 mM EDTA, 5% glycerol, 0.5 mM PMSF, pH 8) and thereafter crushed by French press.

The crushing liquid was centrifuged at 9,000 rpm for 15 minutes, and ammonium sulfate was gradually added to the supernatant so as to be in 40% saturation to precipitate surplus protein. The liquid was left overnight at 4° C. and thereafter centrifuged (9,000 rpm, 4° C., 15 minutes) to collect the supernatant.

Furthermore, ammonium sulfate was gradually added to the supernatant so as to be in 60% saturation to precipitate the target protein. The liquid was left overnight at 4° C. and thereafter centrifuged (9,000 rpm, 4° C., 15 minutes) to collect the precipitates. To the precipitates, 10 ml of buffer B (10 mM phosphoric acid buffer, 1 mM EDTA, 5% glycerol, 0.2 M NaCl, pH 8) was added and dissolved, the buffer was replaced by PD-10 (manufactured by Amersham Corporation), and the solution was then applied to a column (2.8 cm×85 cm) of Ultrogel AcA34 (manufactured by IBF Bio-techniques) previously equilibrated with buffer B. Subsequently, the precipitates were eluted with 1 L of buffer B to collect active fractions.

Concentration of the obtained active fractions was performed by Centriprep-10 (manufactured by Amicon), followed by replacing the buffer by buffer A to apply to a column (1.0 cm×8 cm) of Q-Sepharose FF (manufactured by Amersham Corporation). Elution was achieved by a linear gradient with buffer C (10 mM phosphoric acid buffer, 1 mM EDTA, 5% glycerol, pH 8) through buffer D (10 mM phosphoric acid buffer, 1 mM EDTA, 5% glycerol, 0.5 M NaCl, pH 8). The obtained active fractions were analyzed in SDS-PAGE to observe a single band (molecular weight of about 52,000).

The properties including optimum pH and substrate specificity of the enzymes obtained in such a manner were examined to be similar with those of the enzymes prior to the alteration. That is, the properties, excluding thermal stability, of the eukaryotic amadoriase of the present invention were found to be similar with those of the enzymes prior to the alteration.

EXAMPLE 7

(7) Production of Recombinant Plasmid Encoding Eukaryotic Amadoriase

PCR reaction was performed on conditions described below using phosphorylated primers of SEQ ID NOS: 3 and 4, Pyrobest DNA polymerases (manufactured by Takara Bio Inc.), with DNAs, as templates, of the recombinant plasmid (puc-EFP) (Patent Document 5, FERM BP-8131) of a eukaryotic amadoriase (SEQ ID NO: 2) gene derived from the genus *Eupenicillium*.

That is, 10 μl of 10× Pyrobest buffer solution (manufactured by Takara Bio Inc.), 8 μl of dNTP mixed solution adjusted so that each dNTP was 2.5 mM, 350 ng of DNA of puc-EFP plasmid as a template, 100 pmol of each of the aforementioned primer, and 1 μl of Pyrobest DNA polymerase were added so that the total volume was 100 μl. A thermal cycler (manufactured by Eppendorf Co.) was used to repeat 30 cycles of <94° C., 20 seconds-60° C., 60 seconds-72° C., 120 seconds>.

A part of the reaction liquid was electrophoresed on a 1.0% agarose gel to confirm that about 1,300 bp DNA was specifically amplified.

The eukaryotic amadoriase genes derived from the genus *Eupenicillium* amplified by PCR were linked to pUTE100K' vectors cut with restriction enzymes HpaI (Japanese Patent Application Laid-Open Publication No. 06-292584), and a strain of *E. coli* JM109 was transformed to obtain a recombinant plasmid pUTE100K'-EFP.

The strain of *E. coli* JM109 (pUTE100K'-EFP) possessing the recombinant plasmid pUTE100K'-EFP was shake-cultured in LB-amp medium at a culture temperature of 37° C. for 20 hours to obtain cultures. The obtained culture fungus body was washed and thereafter ultrasonically broken to confirm expression of the activity of eukaryotic amadoriase derived from the genus *Eupenicillium*.

Therefore, the strain of *E. coli* JM109 (pUTE100K'-EFP) was inoculated into 100 ml of LB-amp medium and shake-cultured at a culture temperature of 37° C. for 20 hours to obtain cultures. Harvest of fungi was performed by centrifuging the cultures at 7,000 rpm for 5 minutes to obtain a fungus body.

Using QIAGEN tip-100 (manufactured by Qiagen K.K.), recombinant plasmid pUTE100K'-EFP was extracted and purified from the fungus body to obtain 100 μl of recombinant plasmid pUTE100K'-EFP DNA.

EXAMPLE 8

(8) Site-specific Alteration Operation

A mutation, in which glycine at position 184 in an amino acid sequence according to SEQ ID NO: 2 was replaced by aspartic acid, a mutation, in which asparagine at position 272 was replaced by aspartic acid, and a mutation, in which histidine at position 388 was replaced by tyrosine, were decided to be introduced.

First, in order to introduce a mutation, in which glycine at position 184 in the amino acid sequence according to SEQ ID NO: 2 was replaced by aspartic acid, primers including DNA sequences of SEQ ID NOS: 5 and 6 were synthesized by a usual method. PCR reaction was then performed on the same conditions as in the aforementioned (7) using primers of SEQ ID NOS: 5 and 6, Pyrobest DNA polymerases (manufactured by Takara Bio Inc.), with DNAs, as templates, of the recombinant plasmid pUTE100K'-EFP obtained in the aforementioned (7).

A part of the reaction liquid was analyzed with a 1.0% agarose gel to confirm that about 6,000 bp DNA was specifically amplified. The DNAs obtained in such a manner were treated with a restriction enzyme KpnI following cutting of the remaining templates by restriction enzyme DpnI treatment. The DNAs treated with DpnI and KpnI were electrophoresed on a 1.0% agarose gel, and the DNAs were extracted from the gel by a usual method to collect DNA fragments.

The aforementioned DNA fragments obtained in such a manner were linked using ligase, and a strain of E. coli JM109 was transformed to obtain a recombinant plasmid pUTE100K'-EFP-T1.

Subsequently, in order to introduce a mutation, in which asparagine at position 272 in an amino acid sequence (FPOX-EE) according to SEQ ID NO: 2 was replaced by aspartic acid, PCR reaction was performed on the same conditions as in the aforementioned (7) using primers of SEQ ID NOS: 7 and 8, Pyrobest DNA polymerases (manufactured by Takara Bio Inc.), with Plasmid pUTE100K'-EFP DNAs as templates. The amplified about 6,000 bp DNA was treated with restriction enzymes DpnI and NspV, purified by a usual method, and thereafter ligated, and a strain of E. coli JM109 was transformed to obtain a recombinant plasmid pUTE100K'-EFP-T2.

In order to introduce a mutation, in which histidine at position 388 in an amino acid sequence (FPOX-EE) according to SEQ ID NO: 2 was replaced by tyrosine, PCR reaction was also performed on the same conditions as in the aforementioned (7) using primers of SEQ ID NOS: 9 and 10, Pyrobest DNA polymerases (manufactured by Takara Bio Inc.), with Plasmid pUTE100K'-EFP DNAs as templates. The amplified about 6,000 bp DNA fragments were treated with restriction enzymes DpnI and SnaBI, DNA fragments were purified by a usual method and linked using ligase, and a strain of E. coli JM109 was transformed to obtain a recombinant plasmid pUTE100K'-EFP-T3.

Furthermore, a mutation, in which histidine at position 388 in the amino acid sequence according to the above-mentioned SEQ ID NO: 2 was replaced by tyrosine, was introduced using plasmid pUTE100K'-EFP-T2 DNA as a template to obtain a plasmid pUTE100K'-EFP-T4, and, subsequently, a mutation, in which glycine at position 184 in the amino acid sequence according to the above-mentioned SEQ ID NO: 2 was replaced by aspartic acid, was introduced using plasmid pUTE100K'-EFP-T4 as a template to obtain a plasmid pUTE100K'-EFP-T5.

SEQ ID NO: 5
5'GCT<u>GGTACC</u>TTTCAGCAACCTCTGTTCG 3' (forward primer);

SEQ ID NO: 6
5'AAA<u>GGTACC</u>AGCATCTCCAAAGCCAAACTTG 3' (reverse primer);

(For introduction of G 184D. Underlined portions represent recognition sequences of restriction enzyme KpnI.);

SEQ ID NO: 7
5'TCTT<u>TTTCGAA</u>CCCGACGAGTATGGGGTG 3' (forward primer);

SEQ ID NO: 8
5'TCGGG<u>TTCGAA</u>AAAGAACCCATATTCACC 3' (reverse primer);

(For introduction of N272D. Underlined portions represent recognition sequences of restriction enzyme NspV.);

SEQ ID NO: 9
5'ACATCGGGAAA<u>TACGTA</u>GTTGAGCTTTTAG 3' (forward primer);

SEQ ID NO: 10
5'CTAAAAGCTCAAC<u>TACGTA</u>TTTCCCGATGT 3' (reverse primer);

(For introduction of H388Y. Underlined portions represent recognition sequences of restriction enzyme SnaBI.).

A DNA base sequence encoding a eukaryotic amadoriase in each plasmid was determined using a multi-capillary DNA analysis system CEQ 2000 (manufactured by Beckman Coulter, Inc.).

As a result, mutations, in which glycine at position 184 in an amino acid sequence according to SEQ ID NO: 2 is replaced by aspartic acid in the plasmid pUTE100K'-EFP-T1, asparagine at position 272 in an amino acid sequence according to SEQ ID NO: 2 by aspartic acid in the plasmid pUTE100K'-EFP-T2, histidine at position 388 in an amino acid sequence according to SEQ ID NO: 2 by tyrosine in the plasmid pUTE100K'-EFP-T3, and asparagine at position 272 in an amino acid sequence according to SEQ ID NO: 2 by aspartic acid and histidine at position 388 by tyrosine in the plasmid pUTE100K'-EFP-T4, and a mutation, in which glycine at position 184 in an amino acid sequence according to SEQ ID NO: 2 is replaced by aspartic acid, asparagine at position 272 by aspartic acid, and histidine at position 388 by tyrosine in the plasmid pUTE100K'-EFP-T5, were confirmed to be introduced.

The strains of E. coli JM109 (pUTE100K'-EFP-T1), E. coli JM109 (pUTE100K'-EFP-T2), E. coli JM109 (pUTE100K'-EFP-T3), E. coli JM109 (pUTE100K'-EFP-T4) and E. coli JM109 (pUTE100K'-EFP-T5) possessing the aforementioned recombinant plasmids obtained in such a manner were cultured in LB-amp media at a culture temperature of 37° C. for 20 hours. Each obtained fungus body was washed with a 0.1 M potassium phosphate buffer solution (pH 8.0), thereafter ultrasonically broken, and centrifuged at 15,000 rpm for 10 minutes to prepare 1.5 ml of each crude enzyme solution.

For the enzyme solutions prepared in such a manner, the enzyme activities of remaining amadoriase were measured by the aforementioned method (method of measuring thermal stability). The results are shown in Table 3.

As shown in Table 3, the remaining enzyme activity of the eukaryotic amadoriase prior to the alteration, produced by the strain of E. coli JM109 (pUTE100K'-EFP), in the heat treatment at pH8.0 and 50° C. for 30 minutes, was 2.8% of the activity prior to the heat treatment.

In contrast, the remaining enzyme activities of the eukaryotic amadoriases following the alteration, produced by the strains of E. coli JM109 (pUTE109K'-EFP-T1) and E. coli JM109 (pUTE100K'-EFP-T2), in the heat treatment at pH 8.0 and 50° C. for 30 minutes, were increased to 7.4% and 11.9%, respectively, as compared with the eukaryotic amadoriase prior to the alteration. The remaining enzyme activities of the eukaryotic amadoriases following the alteration, produced by the strains of E. coli JM109 (pUTE109K'-EFP-T3), E. coli JM109 (pUTE100K'-EFP-T4) and E. coli JM109 (pUTE109K'-EFP-T5), in the heat treatment at pH 8.0 and 50° C. for 30 minutes, were further conspicuously increased to 49.7%, 54.8% and 78.9%, respectively, as compared with the eukaryotic amadoriase prior to the alteration.

The eukaryotic amadoriase obtained in the present invention was found to have excellent thermal stability.

TABLE 3

| Plasmid | Mutation | Residual Activity (%) |
|---|---|---|
| pUTE100K'-EFP | — | 2.8 |
| pUTE100K'-EFP-T1 | G184D | 11.9 |
| pUTE100K'-EFP-T2 | N272D | 7.4 |
| pUTE100K'-EFP-T3 | H388Y | 49.7 |
| pUTE100K'-EFP-T4 | N272D, H388Y | 54.8 |
| pUTE100K'-EFP-T5 | G184D, N272D, H388Y | 78.9 |

EXAMPLE 9

(9) Accumulation of Alteration (Production of Quadruple Mutant)

pKK223-3-CFP-T7 includes such mutations that asparagine at position 272 in the amino acid sequence of the eukaryotic amadoriase according to SEQ ID NO: 1 is replaced by aspartic acid, histidine at position 302 by arginine, and histidine at position 388 by tyrosine. A sixfold mutant was decided to be finally made by adding such mutations that arginine at position 94 was replaced by lysine, glycine at 184 by aspartic acid, and phenylalanine at 265 by leucine to the pKK223-3-CFP-T7.

First, in order to introduce a mutation of F265L, primers including DNA sequences of SEQ ID NOS: 11 and 12 were synthesized by a usual method. PCR reaction was then performed on the same conditions as in the aforementioned (7) using primers of SEQ ID NOS: 11 and 12, Pyrobest DNA polymerases (manufactured by Takara Bio Inc.), with the recombinant plasmid pKK223-3-CFP-T7 obtained in the aforementioned (5) as a template.

SEQ ID NO: 11:
'TTCTTCGAACCTGATGAGTTTGGTGTAATAAAG 3' (forward primer)

SEQ ID NO: 12:
5'AGGTTCGAAGAAGAAGCCAAGTTCGCC 3' (reverse primer)

(For Introduction of F265L. Underlined Portions Represent Recognition Sequences of NspV.)

A part of the reaction liquid was analyzed with a 1.0% agarose gel to confirm that about 6 kbp DNA was specifically amplified. The DNAs obtained in such a manner were treated with NspV following cutting of the remaining templates by DpnI treatment. The DNAs treated with DpnI and NspV were electrophoresed on a 1.0% agarose, and the DNAs were extracted and collected from the gel by a usual method. The DNAs obtained in such a manner were ligated, and E. coli JM109 was transformed to obtain a recombinant plasmid pKK223-3-CFP-T8. In addition, as a result of determination of the base sequence of DNA encoding a eukaryotic amadoriase in the pKK223-3-CFP-T8 plasmid using a multi-capillary DNA analysis system CEQ 2000 (manufactured by Beckman Coulter, Inc.), a mutation corresponding to each substitution of F265L, N272D, H302R and H388Y was found to be introduced.

Accumulation of Alteration (Production of Quintuple Mutant)

The recombinant plasmids pKK223-3-CFP-T8 and pKK223-3-CFP-T5 were double-digested with restriction enzymes KpnI and SnaBI. By agarose gel electrophoresis, about 500 bp DNA fragment and about 5.5 kb DNA fragment were dispensed from the pKK223-3-CFP-T8 DNA and pKK223-3-CFP-T5 DNA, respectively, purified by a usual method, and thereafter linked using T4 DNA ligase, and E. coli JM109 was transformed to obtain a recombinant plasmid pKK223-3-CFP-T9.

In addition, as a result of determination of the base sequence of DNA encoding a eukaryotic amadoriase in the pKK223-3-CFP-T9 plasmid using the multi-capillary DNA analysis system CEQ 2000 (manufactured by Beckman Coulter, Inc.), a mutation corresponding to each substitution of G184D, F265L, N272D, H302R and H388Y was found to be introduced.

Accumulation of Alteration (Production of Sixfold Mutant)

The recombinant plasmids pKK223-3-CFP-T9 and pKK223-3-CFP-T4 were digested with a restriction enzyme Bgl II. By agarose gel electrophoresis, about 900 bp DNA fragment and about 5.0 kb DNA fragment were dispensed from the pKK223-3-CFP-T9 DNA and pKK223-3-CFP-T4 DNA, respectively purified by a usual method, and thereafter linked using T4 DNA ligase, and E. coli JM109 was transformed to obtain a recombinant plasmid pKK223-3-CFP-T10. In addition, as a result of determination of the base sequence of DNA encoding a eukaryotic amadoriase in the pKK223-3-CFP-T10 plasmid using the multi-capillary DNA analysis system CEQ 2000 (manufactured by Beckman Coulter; Inc.), a mutation corresponding to each substitution of R94K, G184D, F265L, N272D, H302R and H388Y was found to be introduced.

The plasmid pKK223-3-CFP-T10 manufactured in such a manner was deposited at the Independent Administrative Agency, National Institute of Advanced Industrial Science and Technology, International Patent Organism Depository, in Central 6, 1, Higashi 1-chome, Tsukuba-shi, Ibaraki-ken, Japan, on Mar. 16, 2007, as Deposit No. FERM BP-10800.

The strains of E. coli, JM109 (pKK223-3-CFP-T7), JM109 (pKK223-3-CFP-T8), JM109 (PKK223-3-CFP-T9) and JM109 (pKK223-3-CFP-T10), possessing the recombinant plasmids obtained in such a manner, together with JM109 (PKK223-3-CFP), were cultured in LB-amp media at 37° C. for 20 hours. Each fungus body was washed with a 0.1 M potassium phosphate buffer solution (pH 8.0), thereafter ultrasonically broken, and centrifuged at 15,000 rpm for 10 minutes to prepare 1.5 ml of each crude enzyme solution.

For the enzyme solutions prepared in such a manner, remaining enzyme activities were measured by the aforementioned method (method of measuring thermal stability). The results are shown in Table 4. In Table 4, JM109 (pKK223-3-CFP) represents the eukaryotic amadoriase prior to the alteration, and die enzymes of JM109 (pKK23-3-CFP-T7), JM109 (pKK223-3-CFP-T8), JM109 (pKK223-3-CFP-T9) and JM109 (pKK223-3-CFP-T10) represent the eukaryotic amadoriases of the present invention. As is apparent from this Table 4, the eukaryotic amadoriases obtained in the present invention are found to have the activities that are barely lost even by heat treatment at pH 8.0 and 50° C. for 30 minutes and to have excellent thermal stability.

TABLE 4

| Plasmid | Mutation | Residual Activity (%) After 30 min | After 60 min. |
|---|---|---|---|
| pKK223-3-CFP | — | 6.1 | 3.9 |
| pKK223-3-CFP-T7 | N272D, H302R, H388Y | 95.0 | 83.3 |
| pKK223-3-CFP-T8 | F265L, N272D, H302R, H388Y | 107.7 | 102.4 |
| pKK223-3-CFP-T9 | G184D, F265L, N272D, H302R, H388Y | 112.4 | 108.1 |
| pKK223-3-CFP-T10 | R94K, G184D, F265L, N272D, H302R, H388Y | 117.8 | 105.7 |

EXAMPLE 10

(10) Confirmation of Protease Resistance

The strains of *E. coli*, JM109 (pKK223-3-CFP-T7) and JM109 (pKK223-3-CFP-T10), possessing the recombinant plasmids obtained in up to example 9, together with JM109 (PKK223-3-CFP), were cultured in LB-amp media at 37° C. for 20 hours. Each fungus body was washed with a 0.1 M potassium phosphate buffer solution (pH 8.0), thereafter ultrasonically broken, and centrifuged at 15,000 rpm for 10 minutes to prepare 1.5 ml of each crude enzyme solution.

The crude enzyme solutions were diluted with a 0.1 M phosphate buffer (pH 8.0) so that an amadoriase activity is about 0.05 U/ml, a 50 mU neutral protease (manufactured by Roche Corp.) was added to each sample, and the samples were then warmed at 37° C. for 30 minutes. For each sample, protease resistance was assessed by measuring the activities of the enzymes included in the samples prior to and following the protease treatment and determining percent remaining activities. The results are shown in Table 5. In Table 5, JM109 (pKK223-3-CFP) represents the eukaryotic amadoriase prior to the alteration, and the enzymes of JM109 (pKK223-3-CFP-T7) and JM109 (pKK223-3-CFP-T10) represent the eukaryotic amadoriases of the present invention. As is apparent from this Table 5, the eukaryotic amadoriases obtained in the present invention are found to be significantly improved in resistance to protease and have excellent thermal stability.

TABLE 5

| Plasmid | Mutation | Residual Activity after Protease treatment (%) |
|---|---|---|
| pKK223-3-CFP | — | 1.0 |
| pKK223-3-CFP-T7 | N272D, H302R, H388Y | 43.8 |
| pKK223-3-CFP-T10 | R94K, G184D, F265L, N272D, H302R, H388Y | 108.6 |

The invention claimed is:

1. An eukaryotic amadoriase, consisting of SEQ ID NO:1 with the exception of:
   (a) replacement of asparagine at position 272 of SEQ ID NO:1 by aspartic acid;
   (b) replacement of histidine a position 302 of SEQ ID NO:1 by arginine; and
   (c) replacement of histidine at position 388 of SEQ ID NO:1 by tyrosine.

2. The eukaryotic amadoriase of claim 1, wherein said eukaryotic amadoriase retains at least 83% residual activity after a heat treatment at 50° C. and pH 8.0 for 30 minutes.

3. The eukaryotic amadoriase of claim 1, wherein said eukaryotic amadoriase has an optimal pH between pH 6.0 to pH 8.0.

4. The eukaryotic amadoriase of claim 1, wherein said eukaryotic amadoriase is stable between pH 6.0 to 9.0.

* * * * *

SEQUENCE LISTING

```
<160> NUMBER OF SEQ ID NOS: 17

<210> SEQ ID NO 1
<211> LENGTH: 437
<212> TYPE: PRT
<213> ORGANISM: Coniochaeta sp.

<400> SEQUENCE: 1

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Arg Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Asp Leu Lys Lys Gln Tyr Gln
            100                 105                 110

Ala Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
```

-continued

```
                            180                 185                 190
Phe Asp Asp Glu Gly Thr Thr Cys Ile Gly Val Glu Thr Ala Asp Gly
                195                 200                 205
Thr Lys Tyr Tyr Ala Asp Lys Val Val Leu Ala Ala Gly Ala Trp Ser
            210                 215                 220
Pro Thr Leu Val Asp Leu Glu Asp Gln Cys Cys Ser Lys Ala Trp Val
225                 230                 235                 240
Tyr Ala His Ile Gln Leu Thr Pro Glu Glu Ala Ala Glu Tyr Lys Gly
                245                 250                 255
Val Pro Val Val Tyr Asn Gly Glu Phe Gly Phe Phe Glu Pro Asn
            260                 265                 270
Glu Phe Gly Val Ile Lys Val Cys Asp Glu Phe Pro Gly Phe Ser Arg
            275                 280                 285
Phe Lys Glu His Gln Pro Tyr Gly Ala Pro Ser Pro Lys His Ile Ser
            290                 295                 300
Val Pro Arg Ser His Ala Lys His Pro Thr Asp Thr Tyr Pro Asp Ala
305                 310                 315                 320
Ser Glu Val Ser Ile Lys Lys Ala Ile Ala Thr Phe Leu Pro Arg Phe
                325                 330                 335
Gln Asp Lys Glu Leu Phe Asn Arg Ala Leu Cys Trp Cys Thr Asp Thr
                340                 345                 350
Ala Asp Ala Ala Leu Leu Met Cys Glu His Pro Lys Trp Lys Asn Phe
                355                 360                 365
Ile Leu Ala Thr Gly Asp Ser Gly His Ser Phe Lys Ile Leu Pro Asn
            370                 375                 380
Val Gly Lys His Val Val Glu Leu Ile Glu Gly Arg Leu Pro Glu Glu
385                 390                 395                 400
Met Ala Tyr Gln Trp Arg Trp Arg Pro Gly Gly Asp Ala Leu Lys Ser
                405                 410                 415
Arg Arg Ala Ala Pro Pro Lys Asp Leu Ala Asp Met Pro Gly Trp Lys
                420                 425                 430
His Asp Pro Lys Leu
            435

<210> SEQ ID NO 2
<211> LENGTH: 437
<212> TYPE: PRT
<213> ORGANISM: Eupenicillium terrenum

<400> SEQUENCE: 2

Met Ala His Ser Arg Ala Ser Thr Lys Val Val Val Gly Gly Gly
1               5                   10                  15
Gly Thr Ile Gly Ser Ser Thr Ala Leu His Leu Ile Arg Ser Gly Tyr
                20                  25                  30
Thr Pro Ser Asn Ile Thr Val Leu Asp Val Tyr Lys Thr Pro Ser Leu
            35                  40                  45
Gln Ser Ala Gly His Asp Leu Asn Lys Ile Met Gly Ile Arg Leu Arg
        50                  55                  60
Asn Gly Pro Asp Leu Gln Leu Ser Leu Glu Ser Leu Asp Met Trp Gln
65                  70                  75                  80
Asn Asp Glu Leu Phe Lys Pro Phe Phe His Gln Val Gly Met Ile Asp
                85                  90                  95
Cys Ser Ser Ser Lys Glu Gly Ile Glu Asn Leu Arg Arg Lys Tyr Gln
                100                 105                 110
Thr Leu Leu Asp Ala Gly Ile Gly Leu Glu Lys Thr Asn Val Trp Leu
```

-continued

```
                    115                 120                 125
Glu Ser Glu Asp Glu Ile Leu Ala Lys Ala Pro Asn Phe Thr Arg Glu
130                 135                 140

Gln Val Lys Gly Trp Lys Gly Leu Phe Cys Thr Asp Gly Gly Trp Leu
145                 150                 155                 160

Ala Ala Ala Lys Ala Ile Asn Ala Ile Gly Ile Phe Leu Gln Asp Lys
            165                 170                 175

Gly Val Lys Phe Gly Phe Gly Ala Gly Thr Phe Gln Gln Pro Leu
                180                 185                 190

Phe Ala Ala Asp Gly Lys Thr Cys Ile Gly Leu Glu Thr Thr Asp Gly
            195                 200                 205

Thr Lys Tyr Phe Ala Asp Lys Val Val Leu Ala Ala Gly Ala Trp Ser
    210                 215                 220

Pro Thr Leu Val Asp Leu Glu Asp Gln Cys Val Ser Lys Ala Trp Val
225                 230                 235                 240

Phe Ala His Ile Gln Leu Thr Pro Lys Glu Ala Asp Ala Tyr Lys Asn
                245                 250                 255

Val Pro Val Val Tyr Asp Gly Glu Tyr Gly Phe Phe Phe Glu Pro Asn
            260                 265                 270

Glu Tyr Gly Val Ile Lys Val Cys Asp Glu Phe Pro Gly Phe Ser Arg
        275                 280                 285

Phe Lys Leu His Gln Pro Tyr Gly Ala Ala Ser Pro Lys Met Ile Ser
290                 295                 300

Val Pro Arg Ser His Ala Lys His Pro Thr Asp Thr Tyr Pro Asp Ala
305                 310                 315                 320

Ser Glu Val Thr Ile Arg Lys Ala Ile Ala Arg Phe Leu Pro Glu Phe
                325                 330                 335

Lys Asp Lys Glu Leu Phe Asn Arg Thr Met Cys Trp Cys Thr Asp Thr
            340                 345                 350

Ala Asp Ala Asn Leu Leu Ile Cys Glu His Pro Lys Trp Lys Asn Phe
        355                 360                 365

Ile Leu Ala Thr Gly Asp Ser Gly His Ser Phe Lys Leu Leu Pro Asn
370                 375                 380

Ile Gly Lys His Val Val Glu Leu Leu Glu Gly Ser Leu Ser Gln Glu
385                 390                 395                 400

Met Ala Gly Ala Trp Arg Trp Arg Pro Gly Asp Ala Leu Arg Ser
                405                 410                 415

Arg Arg Gly Ala Pro Ala Lys Asp Leu Ala Glu Met Pro Gly Trp Lys
            420                 425                 430

His Asp Ala His Leu
        435

<210> SEQ ID NO 3
<211> LENGTH: 24
<212> TYPE: DNA
<213> ORGANISM: artificial sequence
<220> FEATURE:
<223> OTHER INFORMATION: primer 3

<400> SEQUENCE: 3
gacatggctc attcgcgtgc aagc                                          24

<210> SEQ ID NO 4
<211> LENGTH: 25
<212> TYPE: DNA
<213> ORGANISM: artificial sequence
<220> FEATURE:
```

<223> OTHER INFORMATION: primer 4

<400> SEQUENCE: 4
caagaatcac aaatgtgcat catgc 25

<210> SEQ ID NO 5
<211> LENGTH: 28
<212> TYPE: DNA
<213> ORGANISM: artificial sequence
<220> FEATURE:
<223> OTHER INFORMATION: G184D primer 5

<400> SEQUENCE: 5
gctggtacct ttcagcaacc tctgttcg 28

<210> SEQ ID NO 6
<211> LENGTH: 31
<212> TYPE: DNA
<213> ORGANISM: artificial sequence
<220> FEATURE:
<223> OTHER INFORMATION: G184D primer 6

<400> SEQUENCE: 6
aaaggtacca gcatctccaa agccaaactt g 31

<210> SEQ ID NO 7
<211> LENGTH: 29
<212> TYPE: DNA
<213> ORGANISM: artificial sequence
<220> FEATURE:
<223> OTHER INFORMATION: N272D primer 7

<400> SEQUENCE: 7 tcttttcga acccgacgag tatggggtg 29

<210> SEQ ID NO 8
<211> LENGTH: 29
<212> TYPE: DNA
<213> ORGANISM: artificial sequence
<220> FEATURE:
<223> OTHER INFORMATION: N272D primer 8

<400> SEQUENCE: 8
tcgggttcga aaagaaccc atattcacc 29

<210> SEQ ID NO 9
<211> LENGTH: 30
<212> TYPE: DNA
<213> ORGANISM: artificial sequence
<220> FEATURE:
<223> OTHER INFORMATION: H338Y primer 9

<400> SEQUENCE: 9
acatcgggaa atacgtagtt gagcttttag 30

<210> SEQ ID NO 10
<211> LENGTH: 30
<212> TYPE: DNA
<213> ORGANISM: artificial sequence
<220> FEATURE:
<223> OTHER INFORMATION: H388Y primer 10

<400> SEQUENCE: 10
ctaaaagctc aactacgtat ttcccgatgt 30

<210> SEQ ID NO 11

-continued

```
<211> LENGTH: 33
<212> TYPE: DNA
<213> ORGANISM: artificial sequence
<220> FEATURE:
<223> OTHER INFORMATION: forward primer

<400> SEQUENCE: 11
ttcttcgaac ctgatgagtt tggtgtaata aag                                33

<210> SEQ ID NO 12
<211> LENGTH: 27
<212> TYPE: DNA
<213> ORGANISM: artificial sequence
<220> FEATURE:
<223> OTHER INFORMATION: reverse primer

<400> SEQUENCE: 12
aggttcgaag aagaagccaa gttcgcc                                       27

<210> SEQ ID NO 13
<211> LENGTH: 440
<212> TYPE: PRT
<213> ORGANISM: Pyrenochaeta sp.

<400> SEQUENCE: 13
```

Met Ala Ala Ser Arg Ala Lys Thr Thr Val Ile Val Gly Gly Gly
1               5                   10                  15

Gly Thr Ile Gly Ser Ser Thr Ala Leu His Leu Leu Arg Ser Gly Tyr
            20                  25                  30

Thr Pro Ser Asn Ile Thr Val Leu Asp Thr Tyr Pro Ile Pro Ser Leu
        35                  40                  45

Gly Ser Ala Gly Asn Asp Leu Asn Lys Ile Met Gly Ile Arg Leu Arg
    50                  55                  60

Asn Lys Val Asp Leu Gln Leu Ser Leu Glu Ala Arg Glu Met Trp Arg
65                  70                  75                  80

Glu Asp Glu Leu Phe Arg Asp Phe Phe His Asn Thr Gly Arg Leu Asp
                85                  90                  95

Cys Ala His Gly Glu Lys Gly Ile Asn Asp Leu Arg Gln Ala Tyr Gln
            100                 105                 110

Thr Leu Leu Asp Ala Asn Ala Gly Leu Glu Glu Thr Asn Glu Trp Leu
        115                 120                 125

Asp Ser Glu Asp Glu Ile Leu Ala Arg Met Pro Leu Leu Ser Arg Glu
    130                 135                 140

Gln Ile Lys Gly Trp Lys Ala Val Phe Ser Arg Asp Gly Gly Trp Leu
145                 150                 155                 160

Ala Ala Gly Lys Ala Ile Asn Ala Ile Gly Glu Tyr Leu Arg Lys Glu
                165                 170                 175

Gly Val Lys Phe Gly Phe Gly Ala Gly Ser Phe Gln Gln Pro Leu
            180                 185                 190

Leu Ala Glu Gly Ile Cys Ile Gly Val Glu Thr Thr Asp Gly Thr Arg
        195                 200                 205

Tyr Tyr Ala Asp Lys Val Val Leu Ala Ala Gly Ala Trp Ser Pro Ala
    210                 215                 220

Leu Val Asp Leu Glu Asp Gln Cys Val Ser Lys Ala Trp Val Tyr Ala
225                 230                 235                 240

His Met Gln Leu Thr Pro Lys Glu Ala Ala Tyr Lys Asp Thr Pro
                245                 250                 255

Val Val Tyr Asn Gly Asp Leu Gly Phe Phe Phe Glu Pro Asn Glu His
            260                 265                 270

```
Gly Val Ile Lys Val Cys Asp Glu Phe Pro Gly Phe Thr Arg Phe Lys
                275                 280                 285

Lys His Gln Pro Phe Gly Ala Arg Ala Pro Lys Arg Ile Ser Val Pro
            290                 295                 300

Arg Ser His Ala Lys His Pro Thr Asp Thr Tyr Pro His Ala Ser Glu
305                 310                 315                 320

Ala Ser Ile Lys Lys Ala Ile Ala Ala Phe Leu Pro Gln Phe Lys Asp
                325                 330                 335

Lys Glu Leu Phe Asn Arg Ala Met Cys Trp Cys Thr Asp Thr Ala Asp
            340                 345                 350

Ala Ala Leu Leu Ile Cys Glu His Pro Gln Trp Lys Asn Phe Met Leu
                355                 360                 365

Ala Thr Gly Asp Ser Gly His Ser Phe Lys Leu Leu Pro Asn Ile Gly
            370                 375                 380

Lys His Val Val Glu Leu Ile Glu Gly Thr Leu Ala Ala Asp Leu Ala
385                 390                 395                 400

His Ala Trp Arg Trp Arg Pro Gly Ile Gly Asp Ala Leu Gln Ser Arg
                405                 410                 415

Arg Ala Ala Pro Ala Lys Asp Leu Ala Asp Met Pro Gly Trp Asn His
            420                 425                 430

Asp Glu Ser Pro Arg Ala Lys Leu
            435                 440

<210> SEQ ID NO 14
<211> LENGTH: 452
<212> TYPE: PRT
<213> ORGANISM: Arthrinium sp.

<400> SEQUENCE: 14

Met Ala Ala Ser Arg Lys Thr Thr Lys Val Ile Val Val Gly Gly Gly
1               5                   10                  15

Gly Thr Ile Gly Ser Ser Thr Ala Leu His Leu Leu Arg Ser Gly Tyr
                20                  25                  30

Thr Ala Thr Asn Ile Thr Val Leu Asp Thr Tyr Pro Ile Pro Ser Ala
            35                  40                  45

Gln Ser Ala Gly Asn Asp Leu Asn Lys Ile Met Gly Ile Arg Leu Arg
        50                  55                  60

Asn Pro Val Asp Lys Gln Leu Ser Leu Glu Ala Gln Asp Met Trp Cys
65                  70                  75                  80

His Asp Glu Leu Phe Lys Pro Tyr Phe His Asn Thr Gly Arg Met Asp
                85                  90                  95

Gly Glu Gly Thr Glu Lys Gly Ile Ala Ala Leu Lys Gln Gln Tyr Gln
            100                 105                 110

Thr Leu Leu Asp Ala Asp Val Gly Leu Glu Lys Thr Thr Glu Trp Leu
        115                 120                 125

Asp Ser Glu Asp Ala Ile Leu Ala Lys Met Pro Leu Leu Glu Arg Asp
    130                 135                 140

Gln Ile Lys Gly Trp Lys Ala Ile Phe Ser Gln Asp Gly Gly Trp Leu
145                 150                 155                 160

Ala Ala Ala Lys Ala Ile Asn Ala Ile Gly Glu Glu Leu Lys Arg Gln
                165                 170                 175

Gly Val Asn Phe Gly Phe Gly Gly Ala Gly Ala Phe Lys Lys Pro Leu
            180                 185                 190

Phe Ala Pro Asp Gly Ser Thr Cys Ile Gly Val Glu Thr Val Asp Gly
        195                 200                 205
```

-continued

```
Thr Lys Tyr Tyr Gly Asp Lys Val Val Leu Ala Ala Gly Ala Trp Ser
    210                 215                 220
Pro Ala Leu Val Asp Leu Glu Glu Gln Cys Cys Ser Lys Ala Trp Val
225                 230                 235                 240
Tyr Ala His Met Gln Leu Thr Pro His Glu Ala Ala Glu Tyr Gln Gly
                245                 250                 255
Cys Pro Val Val Tyr His Gly Asp Leu Gly Phe Phe Phe Glu Pro Asn
            260                 265                 270
Glu His Gly Val Ile Lys Val Cys Asp Glu Phe Pro Gly Phe Thr Arg
        275                 280                 285
Phe Leu Glu Gln His Gln Ser Tyr Gly Ala Pro Ala Pro Thr Arg Val
    290                 295                 300
Ser Val Pro Arg Ser His Ala Lys His Pro Thr Asp Thr Tyr Pro Asp
305                 310                 315                 320
Ala Ser Glu Gln Ser Ile Arg Arg Ala Val Ala Ala Phe Leu Pro Arg
                325                 330                 335
Phe Gln Ser Lys Glu Leu Phe Asn Arg Ala Met Cys Trp Cys Thr Asp
            340                 345                 350
Thr Ala Asp Ala Ala Leu Leu Ile Cys Glu His Pro Arg Trp Arg Asn
        355                 360                 365
Phe Ile Leu Ala Thr Gly Asp Ser Gly His Ser Phe Lys Leu Leu Pro
    370                 375                 380
Asn Ile Gly Lys His Val Val Glu Leu Leu Glu Gly Arg Leu Ala Asp
385                 390                 395                 400
Asp Leu Ala Gln Ala Trp Arg Trp Arg Pro Gly Gln Gly Asp Ala Leu
                405                 410                 415
Lys Ser Arg Arg Ala Ala Pro Ala Lys Asp Leu Ala Asp Met Pro Gly
            420                 425                 430
Trp Asn His Asp Gly Asp Ser Gly Asn Ala Thr Ser Gly Thr Ser Ser
        435                 440                 445
Glu His Lys Leu
    450

<210> SEQ ID NO 15
<211> LENGTH: 441
<212> TYPE: PRT
<213> ORGANISM: Neocosmospora vasinfecta

<400> SEQUENCE: 15

Met Thr Thr Pro Arg Lys Glu Thr Thr Val Leu Ile Ile Gly Gly Gly
1               5                   10                  15
Gly Thr Ile Gly Ser Ser Thr Ala Leu His Leu Leu Arg Ala Gly Tyr
                20                  25                  30
Thr Pro Ser Asn Ile Thr Val Leu Asp Thr Tyr Pro Ile Pro Ser Ala
            35                  40                  45
Gln Ser Ala Gly Asn Asp Leu Asn Lys Ile Met Gly Ile Arg Leu Arg
        50                  55                  60
Asn Lys Val Asp Leu Gln Leu Ser Leu Glu Ala Arg Asp Met Trp Arg
65                  70                  75                  80
Asn Asp Ala Leu Phe Arg Pro Phe Phe His Asn Thr Gly Arg Leu Asp
                85                  90                  95
Cys Glu Ser Ser Ala Glu Gly Val Glu Gly Leu Arg Arg Glu Tyr Gln
            100                 105                 110
Lys Leu Val Glu Ala Gly Val Gly Leu Glu Glu Thr His Glu Trp Leu
        115                 120                 125
```

Asp Ser Glu Glu Ala Ile Leu Glu Lys Ala Pro Leu Leu Gln Arg Glu
    130                 135                 140

Glu Ile Glu Gly Trp Lys Ala Ile Trp Ser Glu Gly Gly Trp Leu
145                 150                 155                 160

Ala Ala Ala Lys Ala Ile Asn Ala Ile Gly Glu Glu Leu Gln Arg Gln
                165                 170                 175

Gly Val Arg Phe Gly Phe Gly Gly Ala Gly Ser Phe Lys Arg Pro Leu
            180                 185                 190

Phe Ala Asp Asp Gly Thr Thr Cys Ile Gly Val Glu Thr Val Asp Gly
        195                 200                 205

Thr Gln Tyr His Ala Asp Lys Val Val Leu Ala Ala Gly Ala Trp Ser
    210                 215                 220

Pro Ala Leu Val Asp Leu Glu Glu Gln Cys Cys Ser Lys Ala Trp Val
225                 230                 235                 240

Tyr Ala His Met Gln Leu Thr Pro Glu Glu Ala Ala Val Tyr Lys Gly
                245                 250                 255

Cys Pro Val Val Tyr His Gly Asp Val Gly Phe Phe Glu Pro Asn
            260                 265                 270

Glu Asn Gly Val Ile Lys Val Cys Asp Glu Phe Pro Gly Phe Thr Arg
        275                 280                 285

Phe Lys Gln His Gln Pro Tyr Gly Ala Pro Ala Pro Lys Pro Val Ser
    290                 295                 300

Val Pro Arg Ser His Ala Lys His Pro Thr Asp Thr Tyr Pro Asp Ala
305                 310                 315                 320

Ser Glu Glu Ser Ile Lys Arg Ala Val Ser Thr Phe Leu Pro Arg Phe
                325                 330                 335

Lys Asp Lys Pro Leu Phe Asn Arg Ala Leu Cys Trp Cys Thr Asp Thr
            340                 345                 350

Ala Asp Ser Ala Leu Leu Ile Cys Glu His Pro Arg Trp Lys Asn Phe
        355                 360                 365

Ile Leu Ala Thr Gly Asp Ser Gly His Ser Phe Lys Leu Leu Pro Ile
    370                 375                 380

Ile Gly Lys His Val Val Glu Leu Val Glu Gly Arg Leu Ala Asp Asp
385                 390                 395                 400

Leu Ala Glu Ala Trp Arg Trp Arg Pro Gly Gln Gly Asp Ala Arg Lys
                405                 410                 415

Ser Ile Arg Ala Ala Pro Ala Lys Asp Leu Ala Asp Met Pro Gly Trp
            420                 425                 430

Lys His Asp Gln Asp Ser Glu Ser Arg
        435                 440

<210> SEQ ID NO 16
<211> LENGTH: 437
<212> TYPE: PRT
<213> ORGANISM: Penicillium janthinellum

<400> SEQUENCE: 16

Met Ala His Ser Arg Glu Ser Thr Lys Ile Val Ile Val Gly Gly Gly
1               5                   10                  15

Gly Thr Met Gly Ser Ser Thr Ala Leu His Leu Ile Arg Ser Gly Tyr
            20                  25                  30

Thr Pro Ser Asn Ile Thr Val Leu Asp Val Tyr Pro Ile Pro Ser Leu
        35                  40                  45

Gln Ser Ala Gly Tyr Asp Leu Asn Lys Ile Met Ser Ile Arg Leu Arg
    50                  55                  60

Asn Gly Pro Asp Leu Gln Leu Ser Leu Glu Ala Leu Asp Met Trp Lys
 65                  70                  75                  80

Asn Asp Pro Leu Phe Lys Pro Phe Phe His Asn Val Gly Arg Leu Asp
             85                  90                  95

Cys Ser Ser Gln Glu Gly Ile Ala Ser Leu Arg Arg Lys His Gln
        100                 105                 110

Asp Leu Ile Asp Ala Asn Ile Gly Leu Glu Lys Thr Asn Ile Trp Leu
            115                 120                 125

Glu Ser Glu Asp Asp Ile Leu Ala Lys Ala Pro His Phe Thr Arg Glu
130                 135                 140

Gln Ile Lys Gly Trp Lys Gly Leu Phe Cys Gly Asp Gly Gly Trp Leu
145                 150                 155                 160

Ala Ala Ala Lys Ala Ile Asn Ala Ile Gly Thr Phe Leu Lys Ser Gln
                165                 170                 175

Gly Val Lys Phe Gly Phe Gly Ser Ala Gly Thr Phe Lys Arg Pro Leu
            180                 185                 190

Phe Ala Pro Asp Gly Ala Thr Cys Ser Gly Val Glu Thr Val Asp Gly
            195                 200                 205

Thr Lys Tyr Phe Ala Asp Lys Val Val Leu Ala Ala Gly Ala Trp Ser
210                 215                 220

Ser Thr Leu Val Asp Leu Glu Asp Gln Cys Val Ser Lys Ala Trp Val
225                 230                 235                 240

Phe Ala His Ile Gln Leu Thr Pro Gln Glu Ser Ala Gln Tyr Lys Asp
                245                 250                 255

Val Pro Val Val Tyr Asp Gly Asp Tyr Gly Phe Phe Glu Pro Asn
            260                 265                 270

Glu His Gly Val Ile Lys Val Cys Asp Glu Phe Pro Gly Phe Ser Arg
            275                 280                 285

Phe Lys Leu His Gln Pro Tyr Gly Ala Thr Ser Pro Lys Glu Ile Ser
290                 295                 300

Val Pro Arg Ser His Ala Lys His Pro Thr Asp Thr Tyr Pro Asp Ser
305                 310                 315                 320

Ser Glu Glu Thr Ile Arg Lys Ala Ile Ala Arg Phe Met Pro Arg Phe
                325                 330                 335

Lys Asp Lys Glu Leu Phe Asn Arg Ser Met Cys Trp Cys Thr Asp Thr
            340                 345                 350

Ala Asp Ala Asn Leu Leu Ile Cys Glu His Pro Lys Trp Lys Asn Phe
            355                 360                 365

Ile Leu Ala Thr Gly Asp Ser Gly His Ser Phe Lys Val Leu Pro Asn
370                 375                 380

Ile Gly Lys His Val Val Glu Leu Ile Glu Gly Arg Leu Pro Gln Asp
385                 390                 395                 400

Leu Ala Gly Ala Trp Arg Trp Arg Pro Gly Gly Asp Ala Leu Lys Ser
                405                 410                 415

Lys Arg Ser Ala Pro Ala Lys Asp Leu Ala Glu Met Pro Gly Trp Lys
            420                 425                 430

His Asp Ala Lys Leu
        435

<210> SEQ ID NO 17
<211> LENGTH: 437
<212> TYPE: PRT
<213> ORGANISM: Aspergillus nidulans

<400> SEQUENCE: 17

```
Met Thr Pro Arg Ala Asn Thr Lys Ile Ile Val Val Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Cys Pro Ile Pro Ser Ala Gln
            35                  40                  45

Ser Ala Gly Tyr Asp Leu Asn Lys Ile Met Ser Ile Arg Leu Arg Asn
        50                  55                  60

Lys Pro Asp Leu Gln Leu Ser Leu Glu Ala Leu Asp Met Trp Lys Asn
65                  70                  75                  80

Asp Pro Leu Phe Lys Pro Phe Phe His Asn Val Gly Met Ile Asp Val
                85                  90                  95

Ser Ser Thr Glu Glu Gly Ile Glu Gly Leu Arg Lys Lys Tyr Gln Ser
            100                 105                 110

Leu Leu Asp Ala Gly Ile Gly Leu Glu Lys Thr Asn Phe Met Leu Glu
        115                 120                 125

Ser Glu Asp Glu Ile Leu Ala Lys Ala Pro His Phe Thr Gln Glu Gln
130                 135                 140

Ile Lys Gly Trp Lys Gly Leu Phe Gly Gly Asp Gly Gly Trp Leu Ala
145                 150                 155                 160

Ala Ala Lys Ala Ile Asn Ala Ile Gly Gln Phe Leu Lys Glu Gln Gly
            165                 170                 175

Val Lys Phe Gly Phe Gly Gly Ala Gly Thr Phe Lys Lys Pro Leu Phe
        180                 185                 190

Ala Asp Ala His Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
            245                 250                 255

Thr Pro Val Ile Tyr Asp Gly Asp Tyr Gly Phe Phe Phe Glu Pro Asn
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Ala Pro Lys Pro Ile Ser
        290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
            325                 330                 335

Asn Asp Lys Glu Leu Phe Asn Arg Ala Met Cys Trp Cys Thr Asp Thr
        340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
370                 375                 380

Ile Gly Lys His Val Val Glu Leu Leu Glu Glu Arg Leu Glu Ser Val
385                 390                 395                 400

Phe Lys Asp Ala Trp Arg Trp Arg Pro Gly Ser Gly Asp Ala Leu Lys
                405                 410                 415
```

```
Ser Arg Arg Ala Ala Pro Ala Lys Asp Leu Ala Asp Met Pro Gly Trp
            420                 425                 430

Arg Asn Glu Ala Lys
            435
```